(12) United States Patent
Cowen et al.

(10) Patent No.: US 6,812,237 B2
(45) Date of Patent: Nov. 2, 2004

(54) N-SUBSTITUTED PEPTIDYL NITRILES AS CYSTEINE CATHEPSIN INHIBITORS

(75) Inventors: Scott Douglas Cowen, Longport, CO (US); Paul David Greenspan, New Providence, NJ (US); Leslie Wighton McQuire, Warren, NJ (US); Ruben Alberto Tommasi, Whitehouse Station, NJ (US); John Henry Van Duzer, Georgetown, MA (US)

(73) Assignee: Novartis AG, Basel (CH)

( * ) Notice: Subject to any disclaimer, the term of this patent is extended or adjusted under 35 U.S.C. 154(b) by 9 days.

(21) Appl. No.: 10/275,583

(22) PCT Filed: May 14, 2001

(86) PCT No.: PCT/EP01/05463

§ 371 (c)(1),
(2), (4) Date: Nov. 7, 2002

(87) PCT Pub. No.: WO01/87828

PCT Pub. Date: Nov. 22, 2001

(65) Prior Publication Data

US 2003/0158256 A1 Aug. 21, 2003

Related U.S. Application Data

(60) Provisional application No. 60/204,217, filed on May 15, 2000.

(51) Int. Cl.[7] ............... A61K 31/445; A61K 31/44; C07D 213/90; C07D 333/22; C07D 305/12
(52) U.S. Cl. ............ 514/320; 514/343; 514/381; 514/391; 514/466; 548/338.1; 548/252; 548/222; 548/253; 548/472; 548/477; 546/113; 546/326; 549/484; 549/466; 549/72; 549/304; 558/392
(58) Field of Search ............... 558/392; 549/72, 549/304, 484, 466; 548/253, 156, 252, 222, 472, 477, 338.1; 546/113, 326; 514/343, 521, 320

(56) References Cited

U.S. PATENT DOCUMENTS

| 3,462,533 A | 8/1969 | Irikura et al. |
| 3,679,730 A | 7/1972 | Irikura et al. |
| 4,260,624 A | 4/1981 | Moore |
| 6,353,017 B1 * | 3/2002 | Altmann et al. ............ 514/428 |

FOREIGN PATENT DOCUMENTS

| WO | WO 92/01675 | 2/1992 |
| WO | WO 99 24460 A | 5/1999 |
| WO | WO 0049007 | 8/2000 |

OTHER PUBLICATIONS

Jean–Pierre Falgueyret et al., Novel, Nonpeptidic Cyanamides as Potent and Reversible Inhibitors of Human Cathepsins K and L, J. Med. Chem. 2001, vol. 44, pp. 94–104.*
John R. Somoza et al., Crystal Structure of Human Cathepsin V., Biochemistry 200, vol. 39, pp. 12543–12551.*
Therese Janecki Delebecq et al., Overexpression Level of Stromelysin 3 Is Related to the Lymph Node Involvement in Non–small Cell Lung Cancer, Clinical Cancer Research, vol. 6, pp. 1086–1092, 2000.*
Paul D. Greenspan et al., N–Arylaminonitriles as Bioavailable Peptidomimetic Inhibitors of Cathepsin B; Biorganic & Medicinal Chemistry Letters vol. 13, 2003, pp. 4121–4124.*
Suzue S. et al., Chemical & Pharmaceutical Bulletin, vol. 16, No. 8 (1968).
Chemical Abstract 1969:437778 CAPLUS.
Chemical Abstracts 106:14732 (1987)—Abstract of JP 61152646.

* cited by examiner

*Primary Examiner*—Johann Richter
*Assistant Examiner*—Ebenezer Sackey
(74) *Attorney, Agent, or Firm*—Edward J. Wilusz

(57) ABSTRACT

Compounds of the formula (I), wherein $R_1$ is aryl or biaryl; $R_2$ is aryl-lower alkyl, biaryl-lower alkyl, benzo-fused cycloalkyl, cycloalkyl-lower alkyl, bicycloalkyl-lower alkyl, aryloxy-lower alkyl, or aryl-$C_2$–$C_7$-alkyl in which $C_2$–$C_7$-alkyl is interrupted by Y; Y is O, S, SO, $SO_2$, CO or $NR_6$; $R_3$ is hydrogen or lower alkyl; or $R_2$ and $R_3$ combined are $C_2$–$C_7$-alkylene or $C_2$–$C_7$-alkylene interrupted by Y; $R_4$ is hydrogen or lower alkyl; $R_5$ is hydrogen, optionally substituted lower alkyl, aryl-lower alkyl, biaryl-lower alkyl, cycloalkyl-lower alkyl, bicycloalkyl-lower alkyl, aryloxy-lower alkyl, or aryl-$C_2$–$C_7$-alkyl in which $C_2$–$C_7$-alkyl is interrupted by Y; $R_6$ is hydrogen, lower alkyl or aryl-lower alkyl; and pharmaceutically acceptable salts thereof, which are useful as cysteine cathepsin inhibitors (I)

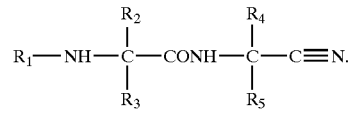

16 Claims, No Drawings

N-SUBSTITUTED PEPTIDYL NITRILES AS CYSTEINE CATHEPSIN INHIBITORS

This application claims the benefit of provisional application No. 60/204,217, filed May 15, 2000.

SUMMARY OF THE INVENTION

This invention relates to novel cysteine cathepsin inhibitors and their pharmaceutical use for the treatment or prophylaxis of diseases or medical conditions in which cathepsins are implicated.

The cysteine cathepsins, e.g. cathepsins B, L and S, are a class of lysosomal enzymes which are implicated in various disorders including inflammation, rheumatoid arthritis, osteoarthritis, osteoporosis, tumors (especially tumor invasion and tumor metastasis), coronary disease, atherosclerosis (including atherosclerotic plaque rupture and destabilization), autoimmune diseases, respiratory diseases (including asthma and chronic obstructive pulmonary disease), infectious diseases and immunologically mediated diseases (including transplant rejection).

The compounds of the invention are particularly useful as cathepsin inhibitors, primarily as cathepsin B inhibitors, and can be used for the treatment of the above-cited cathepsin dependent conditions.

DETAILED DESCRIPTION OF THE INVENTION

The invention relates to the novel cathepsin inhibitors of the formula

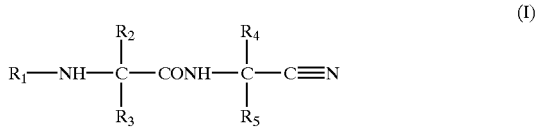

(I)

wherein $R_1$ is aryl or biaryl;

$R_2$ is aryl-lower alkyl, biaryl-lower alkyl, benzo-fused cycloalkyl, cycloalkyl-lower alkyl, bicycloalkyl-lower alkyl, aryloxy-lower alkyl, or aryl-$C_2$–$C_7$-alkyl in which $C_2$–$C_7$-alkyl is interrupted by Y;

Y is O, S, SO, $SO_2$, CO or $NR_6$;

$R_3$ is hydrogen or lower alkyl; or $R_2$ and $R_3$ combined are $C_2$–$C_7$-alkylene or $C_2$–$C_7$-alkylene interrupted by Y;

$R_4$ is hydrogen or lower alkyl;

$R_5$ is hydrogen, optionally substituted lower alkyl, aryl-lower alkyl, biaryl-lower alkyl, cycloalkyl-lower alkyl, bicycloalkyl-lower alkyl, aryloxy-lower alkyl, or aryl-$C_2$–$C_7$-alkyl in which $C_2$–$C_7$-alkyl is interrupted by Y;

$R_6$ is hydrogen, lower alkyl or aryl-lower alkyl;

and pharmaceutically acceptable salts thereof.

A particular embodiment of the invention relates to the compounds of formula I wherein $R_5$ represents the grouping

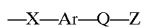

in which X is lower alkylene, lower alkyleneoxy or $C_2$–$C_7$-alkylene interrupted by Y; Ar is monocyclic carbocyclic or monocyclic heterocyclic arylene; Q is a direct bond, lower alkylene, or thio- or oxy-lower alkylene: Z is hydroxy, acyloxy, carboxyl, or carboxyl derivatized as a pharmaceutically acceptable ester or amide; or Z is 5-tetrazolyl; Y is O, S, SO, $SO_2$ or $NR_6$; and $R_6$ is hydrogen, lower alkyl or aryl-lower alkyl; and pharmaceutically acceptable salts thereof.

A specific embodiment of the invention relates to the compounds of formula II

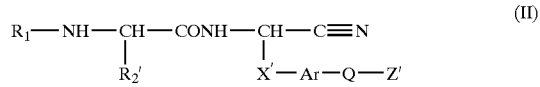

(II)

wherein $R_1$ is aryl or biaryl;

$R'_2$ aryl-lower alkyl, biaryl-lower alkyl, benzo-fused cycloalkyl, cycloalkyl-lower alkyl or bicycloalkyl-lower alkyl;

Ar is monocyclic carbocyclic or monocyclic heterocyclic arylene;

X' is lower alkylene or $C_2$–$C_7$-alkylene interrupted by Y';

Y' is O or S;

Q is a direct bond, lower alkylene, or thio- or oxy-lower alkylene; and

Z' is carboxyl, carboxyl derivatized as a pharmaceutically acceptable ester or amide, 5-tetrazolyl, or hydroxymethyl;

and pharmaceutically acceptable salts thereof.

A specific embodiment of the invention is directed to compounds of formula II wherein $R_1$ is aryl; $R'_2$ is aryl-lower alkyl, X' is $C_1$–$C_5$-alkylene, or X' is $C_2$–$C_4$-alkylene interrupted by O or S; Ar is monocyclic carbocyclic arylene; Q is a direct bond, oxy-$C_1$–$C_4$-alkylene or $C_1$–$C_4$-alkylene; and Z' is carboxyl or carboxyl derivatized as a pharmaceutically acceptable ester; and pharmaceutically acceptable salts thereof.

A more specific embodiment of the invention is directed to compounds of formula If wherein $R_1$ is monocyclic carbocyclic aryl; $R'_2$ is carbocyclic aryl-methyl; X' is $C_1$–$C_3$-alkylene; or X' is $C_2$-alkylene interrupted by O; Ar is monocarbocyclic arylene; Q is a direct bond or oxymethylene; Z' is carboxyl, carboxyl derivatized as a pharmaceutically acceptable ester, or 5-tetrazolyl; and pharmaceutically acceptable salts thereof.

A particular embodiment of the invention relates to the compounds of the formula IIa

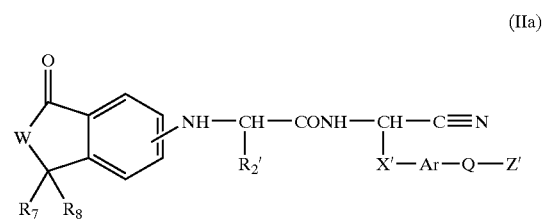

(IIa)

wherein $R'_2$, X', Ar, Q and Z' have meaning as defined above, W represents O, $CH_2$ or $NR_6$ in which $R_6$ is lower alkyl; and $R_7$ and $R_8$ independently represent hydrogen or lower alkyl; or $R_7$ and $R_8$ together represent oxo; and pharmaceutically acceptable salts thereof.

Another embodiment of the invention relates to compounds of formula III

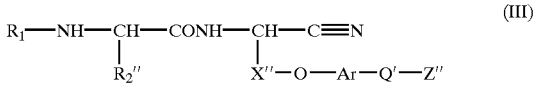

wherein
- R₁ is aryl or biaryl;
- R"₂ is aryl-lower alkyl, biaryl-lower alkyl, cycloalkyl-lower alkyl or bicycloalkyl-lower alkyl;
- Ar is monocyclic carbocyclic or monocyclic heterocyclic arylene;
- X" is lower alkylene;
- Q' is a direct bond or lower alkylene;
- Z" is carboxyl, carboxyl derivatized as a pharmaceutically acceptable ester, or 5-tetrazolyl;

and pharmaceutically acceptable salts thereof.

A specific embodiment of the invention relates to compounds of formula III wherein R₁ is monocyclic carbocyclic or heterocyclic aryl; R"₂ is aryl-lower alkyl; Q' is a direct bond or lower alkylene; and Z" is carboxyl; and pharmaceutically acceptable salts thereof.

A more specific embodiment relates to the compounds of formula III wherein R₁ is monocyclic carbocyclic aryl; R"₂ is carbocyclic aryl-methyl; X" is C₃-alkylene; Ar is monocyclic carbocyclic arylene; Q' is a direct bond; Z" is carboxyl; and pharmaceutically acceptable salts thereof.

The compounds of the invention depending on the nature of substituents, possess one or more asymmetric carbons. The resulting diastereomers and enantiomers are encompassed by the instant invention.

Preferred are the compounds of the invention wherein the asymmetric carbon to which are attached R₂ and/or R₃ corresponds to that of an L-amino acid precursor and the asymmetric carbon to which is attached the cyano group also corresponds to that of an L-amino acid; both asymmetric centers are typically assigned the (S)-configuration. As an illustration, the preferred compounds of the formula I wherein R₃ and R₄ represent hydrogen can be represented by formula IV

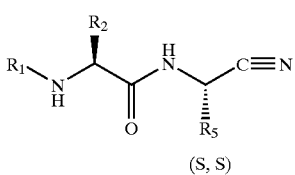

(S, S)

wherein R₁, R₂ and R₅ have meaning as previously defined. Particularly preferred are the compounds of the formula V

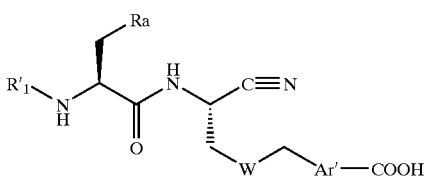

wherein R'₁ and Ra are aryl; W is O or CH₂; Ar' is arylene selected from pyridylene, furanylene, thienylene, thiazolylene, phenylene or phenylene substituted by 1 to 3 of alkyl or halo; pharmaceutically acceptable salts thereof; and pharmaceutically acceptable esters thereof.

Further preferred are the compounds of formula V wherein R'₁ and Ra are independently phthalidyl, phenyl, or phenyl mono-, di- or tri-substituted by lower alkyl, halo, trifluoromethyl, cyano, nitro, hydroxy, acyloxy, acyl, carboxyl, lower alkylsulfonyl, or esterified or amidated carboxyl; W is O; Ar' is 1,3-phenylene or 1,3-phenylene mono- or di-substituted by chloro or fluoro; pharmaceutically acceptable salts thereof; and pharmaceutically acceptable esters thereof.

Especially preferred are the compounds of formula V wherein R'₁ is phthalidyl, phenyl, or phenyl mono- or disubstituted by halo, lower alkyl or esterified or amidated carboxyl; Ra is 3-tolyl; W is O; Ar' is 1,3-phenylene or 1,3-phenylene mono- or disubstituted by chloro or fluoro; pharmaceutically acceptable salts thereof; and pharmaceutically acceptable esters thereof.

Further preferred are the compounds of formula V wherein R'₁ is phenyl; Ra is 3-tolyl; W is O; Ar' is 1,3-phenylene or 1,3-phenylene mono- or disubstituted by chloro or fluoro; pharmaceutically acceptable salts thereof; and pharmaceutically acceptable esters thereof.

The general definitions used herein have the following meaning within the scope of the invention, unless otherwise specified.

The term "lower" referred to above and hereinafter in connection with organic radicals or compounds respectively defines such as branched or unbranched with up to and including 7, preferably up to and including 4 and advantageously one or two carbon atoms.

Alkyl represents $C_1$–$C_{20}$-alkyl, preferably lower alkyl, which may be substituted as described below.

Optionally substituted lower alkyl refers to unsubstituted or substituted straight or branched chain hydrocarbon groups having 1 to 7 carbon atoms, preferably 1 to 4 carbon atoms. Substituted lower alkyl groups include, but are not limited to, alkyl groups substituted by one or more of the following groups: halo, hydroxy, acyloxy, alkoxy, amino, alkylamino, dialkylamino, acylamino, mercapto, alkylthio, alkylsulfinyl, alkylsulfonyl, arylsulfonyl (including heteroarylsulfonyl), aminosulfonyl, nitro, cyano, carboxyl, alkoxycarbonyl, pyrrolidyl, piperidyl, morpholinyl, (alkyloxy, carboxy, alkoxycarbonyl)-alkoxy, and the like.

A lower alkyl group is branched or unbranched and contains 1 to 7 carbon atoms, preferably 1–4 carbon atoms. Lower alkyl represents for example methyl, ethyl, propyl, butyl, isopropyl or isobutyl.

Lower alkylene represents either straight chain or branched alkylene of 1 to 7 carbon atoms and represents preferably straight chain alkylene of 1 to 4 carbon atoms, e.g. a methylene, ethylene, propylene or butylene chain, or said methylene, ethylene, propylene or butylene chain mono-substituted by $C_1$–$C_3$-alkyl (advantageously methyl) or disubstituted on the same or different carbon atoms by $C_1$–$C_3$-alkyl (advantageously methyl), the total number of carbon atoms being up to and including 7.

A lower alkoxy (or alkyloxy) group preferably contains 1–4 carbon atoms, advantageously 1–3 carbon atoms, and represents for example ethoxy, propoxy, isopropoxy, or most advantageously methoxy.

Halogen (halo) preferably represents chloro or fluoro but may also be bromo or iodo.

Aryl represents carbocyclic or heterocyclic aryl.

Carbocyclic aryl represents monocyclic or bicyclic aryl, for example phenyl or phenyl mono-, di- or tri-substituted by one, two or three radicals selected from optionally substituted lower alkyl, lower alkoxy, hydroxy, amino, halogen, cyano and trifluoromethyl, or substituted by $C_3$–$C_5$- alkylene, lower alkylenedioxy or oxy-$C_2$–$C_3$-alkylene on adjacent carbon atoms; or 1- or 2-naphthyl. Lower alkylenedioxy is a divalent substituent attached to two adjacent carbon atoms of phenyl, e.g. methylenedioxy or ethylenedioxy. Oxy-$C_2$–$C_3$-alkylene is also a divalent substituent attached to two adjacent carbon atoms of phenyl, e.g. oxyethylene or oxypropylene. An example for oxy-$C_2$–$C_3$-alkylene substituted phenyl is 2,3-dihydrobenzofuran-5-yl. Alkylene substituted phenyl is e.g. indanyl or tetralinyl.

Preferred as carbocyclic aryl is phenyl or phenyl mono- or disubstituted by lower alkoxy, halogen, lower alkyl or trifluoromethyl, especially phenyl or phenyl monosubstituted by lower alkoxy, halogen or trifluoromethyl, and in particular phenyl.

Heterocyclic aryl represents monocyclic or bicyclic heteroaryl, for example pyridyl, indolyl, isoindolyl, quinoxalinyl, quinolinyl, isoquinolinyl, benzothienyl, benzofuranyl, benzopyranyl, benzothiopyranyl, furanyl, pyrrolyl, thiazolyl, oxazolyl, isoxazolyl, triazolyl, tetrazolyl, pyrazolyl, imidazolyl, thienyl, or any said radical substituted, especially mono- or di-substituted, by e.g. lower alkyl, lower alkoxy or halogen. Pyridyl represents 2-, 3- or 4-pyridyl. Thienyl represents 2- or 3-thienyl. Quinolinyl represents preferably 2-, 3- or 4-quinolinyl. Isoquinolinyl represents preferably 1-, 3- or 4-isoquinolinyl. Benzopyranyl, benzothiopyranyl represent preferably 3-benzopyranyl or 3-benzothiopyranyl, respectively. Thiazolyl represents preferably 2- or 4-thiazolyl. Triazolyl is preferably 1-, 2- or 5-(1,2,4-triazolyl). Tetrazolyl is preferably 5-tetrazolyl.

Preferably, heterocyclic aryl is pyridyl, indolyl, quinolinyl, pyrrolyl, thiazolyl, isoxazolyl, triazolyl, tetrazolyl, pyrazolyl, imidazolyl, thienyl, or any said radical substituted, especially mono- or di-substituted, by lower alkyl or halogen; and in particular pyridyl.

Aryl, for example in conjunction with $R_1$, also represents a grouping of the general formula

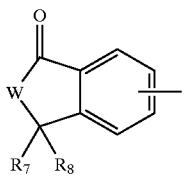

wherein W is O, $CH_2$ or $NR_6$; $R_6$, $R_7$ and $R_8$ represent independently hydrogen or lower alkyl; or $R_7$ and $R_8$ combined represent oxo; and the line represents the point of attachment. Illustrative thereof is 3-oxo-1,3-dihydrobenzofuran-5-yl (5-phthalidyl).

Aryl, for example in conjunction with $R_5$, also represents a heterocyclic or carbocyclic aromatic ring system as defined above which is substituted by the grouping —Q—Z in which Q is a direct bond, lower alkylene, or thio- or oxy-lower alkylene; and Z is hydroxy, acyloxy, carboxyl or carboxyl derivatized as a pharmaceutically acceptable ester or amide; or Z is 5-tetrazolyl.

Arylene (Ar in formula II) is an aryl linking group in which aryl is monocyclic heterocyclic or carbocyclic aryl.

A heterocyclic aryl linking group is for instance (but not limited thereto) 1,3-pyrazolyl, 2,4- or 2,6-pyridyl, 2,5-thienyl, 2,4-thiazolyl, 2,5-furanyl or 1,4-imidazolyl in which the groups as depicted in formula II are attached to the ring at the indicated positions.

A carbocyclic aryl linking group is for instance (but not limited thereto) optionally substituted phenyl and in which the two groups as depicted in formula II are attached ortho, meta or para to each other, preferably meta. Optional substituents are e.g. halo, alkyl and the like.

Biaryl is preferably carbocyclic biaryl, e.g. biphenyl, namely 2-, 3- or 4-biphenyl, advantageously 4-biphenyl, each optionally substituted by e.g. lower alkyl, lower alkoxy, halogen, trifluoromethyl or cyano.

Cycloalkyl represents a saturated cyclic hydrocarbon optionally substituted by lower alkyl which contains 3 to 10 ring carbons and is advantageously cyclopentyl, cyclohexyl, cycloheptyl or cyclooctyl optionally substituted by lower alkyl.

Benzo-fused cycloalkyl represents for example indanyl, tetralinyl and the like.

Bicycloalkyl is for example norbornanyl.

Aryl-lower alkyl represents (carbocyclic aryl or heterocylic aryl)-lower alkyl.

Carbocyclic aryl-lower alkyl represents preferably straight chain or branched aryl-$C_{1-4}$-alkyl in which carbocyclic aryl has meaning as defined above, e.g. benzyl or phenyl-(ethyl, propyl or butyl), each unsubstituted or substituted on phenyl ring as defined under carbocyclic aryl above, advantageously optionally substituted benzyl, e.g. benzyl substituted by lower alkyl, lower alkoxy and the like.

Heterocyclic aryl-lower alkyl represents preferably straight chain or branched heterocyclic aryl-$C_{1-4}$-alkyl in which heterocyclic aryl has meaning as defined above, e.g. 2-, 3- or 4-pyridylmethyl or (2,3- or 4-pyridyl)-(ethyl, propyl or butyl); or 2- or 3-thienylmethyl or (2- or 3-thienyl)-(ethyl, propyl or butyl); 2-, 3- or 4-quinolinylmethyl or (2-, 3- or 4-quinolinyl)-(ethyl, propyl or butyl); or 2- or 4-thiazolylmethyl or (2- or 4-thiazolyl)-(ethyl, propyl or butyl); 3-indolylmethyl or 3-indolyl-(ethyl, propyl or butyl); 2- or 3-furanylmethyl; and said heterocyclic aryl group being optionally substituted by e.g. lower alkyl or lower alkoxy.

Cycloalkyl-lower alkyl represents e.g. (cyclopentyl- or cyclohexyl)-(methyl or ethyl).

Biaryl-lower alkyl represents e.g. 4-biphenylyl-(methyl or ethyl).

Acyl as in acyloxy is derived from an organic carboxylic acid, carbonic acid or carbamic acid. Acyl represents e.g. lower alkanoyl, carbocyclic aryl-lower alkanoyl, lower alkoxycarbonyl, aroyl, di-lower alkylaminocarbonyl or di-lower alkylamino-lower alkanoyl. Preferably, acyl is lower alkanoyl.

Lower alkanoyl represents e.g. $C_{1-7}$-alkanoyl including formyl, and is preferably $C_{2-4}$-alkanoyl such as acetyl or propionyl.

Aroyl represents e.g. benzoyl or benzoyl mono- or di-substituted by one or two radicals selected from lower alkyl, lower alkoxy, halogen, cyano and trifluoromethyl; or 1- or 2-naphthoyl; and also e.g. pyridylcarbonyl.

Lower alkoxycarbonyl represents preferably $C_{1-4}$-alkoxycarbonyl, e.g. ethoxycarbonyl.

Carboxyl derivatized as a pharmaceutically acceptable ester is for example an optionally substituted lower alkyl ester, such as lower alkoxycarbonyl.

Carboxyl derivatized as a pharmaceutically acceptable amide is for example aminocarbonyl, mono- or di-lower alkylaminocarbonyl.

Pharmaceutically acceptable salts of the acidic compounds of the invention are salts formed with bases, namely cationic salts such as alkali and alkaline earth metal salts, such as sodium, lithium, potassium, calcium, magnesium, as well as ammonium salts, such as ammonium, trimethylammonium, diethylammonium, and tris-(hydroxymethyl)-methyl-ammonium salts.

Similarly acid addition salts, such as of mineral acids, organic carboxylic and organic sulfonic acids e.g. hydrochloric acid, methanesulfonic acid, maleic acid, are also possible provided a basic group, such as pyridyl, constitutes part of the structure.

The compounds of the invention exhibit valuable pharmacological properties in mammals including man and are particularly useful as cysteine cathepsin inhibitors.

As the compounds of the invention are inhibitors of cysteine cathepsin enzymes, they are particularly useful in mammals as agents for the treatment of e.g. osteoarthritis, rheumatoid arthritis, tumor metastasis, and atherosclerotic plaque rupture and plaque destabilization.

Beneficial effects are evaluated in in vitro and in vivo pharmacological tests generally known in the art, and as illustrated herein.

The above cited properties are demonstrable in in vitro and in vivo tests, using advantageously mammals, e.g. rats, mice, dogs, or isolated organs and tissues, as well as mammalian enzyme preparations, either natural or prepared by e.g. recombinant technology. Said compounds can be applied in vitro in the form of solutions, e.g. preferably aqueous solutions or suspensions, and in vivo either enterally or parenterally, advantageously orally, e.g. as a suspension or in aqueous solution, or as a solid capsule formulation. The dosage in vitro may range between about $10^{-5}$ molar and $10^{-9}$ molar concentrations. The dosage in vivo may range, depending on the route of administration, between about 0.1 and 100 mg/kg.

The cathepsin inhibitory effects of the compound of the invention can be determined in vitro by measuring the inhibition of e.g. recombinant human cathepsins B, L and S. The buffer used in the assays is a 0.1 M pH 5.8 phosphate buffer containing EDTA (1.33 mM), DTT (2.7 mM) and Brij (0.03%).

The in vitro assays are carried out as follows:

(a) For Cathepsin B:

To a microtiter well is added 100 uL of a 20 uM solution of inhibitor in assay buffer followed by 50 uL of a 6.4 mM solution of Z—Arg—Arg—AMC substrate (Peptides International) in assay buffer. After mixing, 50 uL of a 0.544 nM solution of recombinant human cathepsin B in assay buffer is added to the well, yielding a final inhibitor concentration of 10 uM. Enzyme activity is determined by measuring fluorescence of the liberated aminomethylcoumarin at 440 nM using 380 nM excitation, at 20 minutes. % Enzyme inhibition is determined by comparison of this activity to that of a solution containing no inhibitor. Compounds are subsequently subjected to a dose response curve analysis to determine $IC_{50}$ values.

(b) For Cathepsin L:

Recombinant human cathepsin L is activated prior to use in this assay: To 500 uL of a 510 nM solution of cathepsin L in a 50 mM pH 5.0 acetate buffer containing 1 mM EDTA, 3 mM DTT and 150 mM NaCl is added 10 uL of a 625 uM solution of dextran sulfate (ave. mw=8000), and the resulting solution is incubated on ice for 30 min. 4 uL of this solution is then diluted into 46 uL assay buffer, yielding a 40 nM enzyme solution.

To perform the assay, 100 uL of a 20 uM solution of inhibitor in assay buffer is added to a microtiter well. 50 uL of a 20 uM solution of Z-Phe-Arg-AMC (Peptides International) is then added. After mixing, 50 uL of the activated 40 nM solution of recombinant human cathepsin L in assay buffer is then added to the well, yielding a final inhibitor concentration of 10 uM. Enzyme activity is determined by measuring fluorescence of the liberated aminomethylcoumarin at 440 nM using 380 nM excitation of 20 minutes. % Enzyme inhibition is determined by comparison of this activity to that of a solution containing no inhibitor. Compounds are subsequently subjected to a dose response curve analysis to determine $IC_{50}$ values.

(c) For Cathepsin S:

To a microtiter well is added 100 uL of a 20 uM solution of inhibitor is assay buffer. 50 uL of a 700 uM solution of Z-Val-Val-Arg-AMC substrate (Peptides International) is then added. After mixing, 50 uL of a 5.2 nM solution of recombinant human cathepsin S in assay buffer is then added to the well, yielding a final inhibitor concentration of 10 uM. Enzyme activity is determined by measuring fluorescence of the liberated aminomethylcoumarin at 440 nM using 380 nM excitation at 200 minutes. % Enzyme inhibition is determined by comparison of this activity to that of a solution containing no inhibitor. Compounds are subsequently subjected to a dose response curve analysis to determine $IC_{50}$ values.

Compounds of the invention, primarily those in which $R_5$ represents the grouping —X—Ar—Q—Z, are typically selective cathepsin B inhibitors. $IC_{50}$ values may range between about 10 and 1000 nM, preferably between about 10 and 200 nM.

Illustrative of the invention, the $IC_{50}$ in the in vitro cathepsin B assay is about 100 nM for the compound of example 6.

The antiarthritic efficacy of the compounds of the invention for the treatment of rheumatoid arthritis can be determined using the rat model of adjuvant arthritis, as described previously (R. E. Esser, et. al. *J. Rheumatology*, 1993, 20, 1176.)

The efficacy of the compounds of the invention for the treatment of osteoarthritis can be determined using the rabbit partial lateral meniscectomy model, as described previously (Colombo et al. *Arth. Rheum.* 1993 26, 875–886). The efficacy of the compounds in the model can be quantified using histological scoring methods, as described previously (O'Byrne et al. *Inflamm Res* 1995, 44, S117–S118).

The compounds of the invention are prepared by:

(a) condensing a compound of the formula VI

(VI)

wherein $R_4$ and $R_5$ have meaning as defined herein, with an acid of formula VII

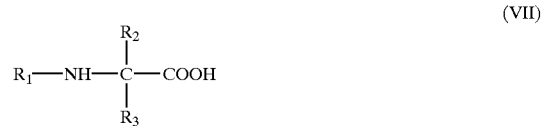

(VII)

wherein $R_1$, $R_2$ and $R_3$ have meaning as defined above; or with a reactive derivative thereof; or (b) condensing a compound of the formula VIII

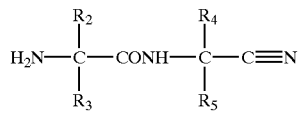
(VIII)

wherein $R_2$, $R_3$, $R_4$, and $R_5$ have meaning as defined herein, with a reactive aryl reagent corresponding to the aryl group $R_1$; and in above processes, if required, temporarily protecting any interfering reactive groups and then isolating the resulting compound of the invention; and, if desired, converting any resulting compound into another compound of the invention; and/or if desired, converting a resulting compound into a salt or a resulting salt into the free acid or base or into another salt.

In starting compounds and intermediates, which are converted to the compounds of the invention in a manner described herein, functional groups present such as amino, hydroxy and carboxyl groups, are optionally protected by conventional protecting groups that are common in preparative organic chemistry. Protected hydroxy, amino and carboxyl groups are those that can be converted under mild conditions into free amino, hydroxy and carboxyl groups without other undesirable side reactions taking place. For example, carboxyl protecting groups are allyl, benzyl or substituted benzyl groups, and the like.

The preparation of any nitrile intermediates from the corresponding primary amides, can be carried out according to methods well known in the art for the dehydration of a primary amide to a nitrile, e.g. with thionyl chloride or oxalyl chloride in the presence of a base. A preferred procedure involves the treatment with oxalyl chloride and pyridine in DMF at or below room temperature.

The starting materials of formula VIII can be prepared by condensing a nitrile of formula VI with a protected amino acid of formula IX

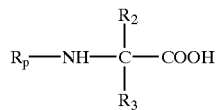
(IX)

wherein $R_2$ and $R_3$ have meaning as defined herein and Rp is an amino protecting group, preferably 1-butoxycarbonyl.

The condensation can be carried out according to methods well-known in the art, e.g. by reacting a nitrile of formula VI with a protected amino acid of formula IX in the presence of a condensing agent such as N-(3-dimethylaminopropyl)-N'-ethylcarbodiimide, optionally in the presence of e.g. hydroxybenzotriazole or 1-hydroxy-7-azabenzotriazole, and a base such as N-methylmorpholine, followed by deprotection (e.g. with formic acid) of the t-butoxycarbonyl (Boc) group.

The protected amino acids of formula IX and aminonitriles of formula VI are either known or can be prepared according to methodology known in the art and illustrated herein.

N-Arylaminoacids of formula VII can be prepared through reaction of the appropriate aryl iodide with an amino acid or aminoacid HCl salt, in the presence of Pd(Oac)$_2$, CuI, TEBA, K$_2$CO$_3$, DMF, water, triethylamine and tri-o-tolylphosphine, as described in *Tetrahedron: Asymmetry* 1996, 7, 3075. Aryl iodides are either commercially available, or are prepared from the corresponding aniline, using standard procedures (NaNO$_2$,HCl, KI).

The optically active N-arylaminoacids of formula VII can also be prepared through conversion of the ester of the opposite enantiomer of the amino acid to its corresponding α-hydroxyester, followed by triflation, arylamine displacement, and ester hydrolysis as illustrated below:

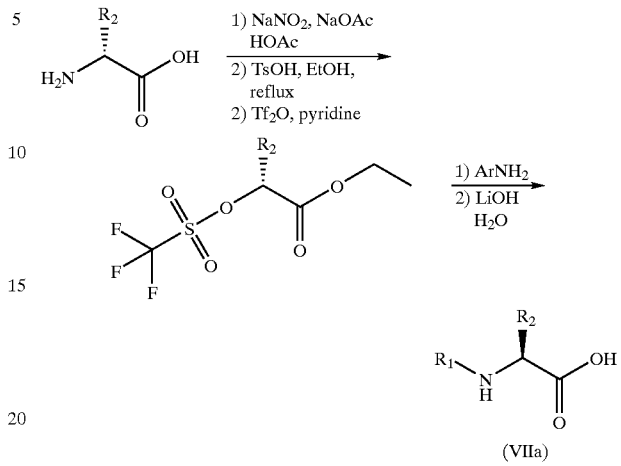
(VIIa)

Aminonitriles of formula VI and prepared e.g. through conversion of the Boc-protected amino acid to its corresponding primary amide, followed by dehydration, using thionyl chloride, oxalyl chloride or some other dehydrating reagent, and then Boc deprotection using formic acid as illustrated below.

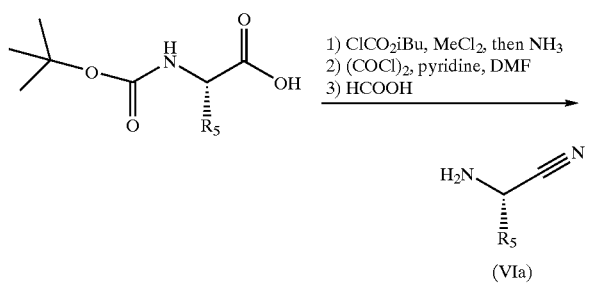
(VIa)

For example, the compounds of formula VIa wherein $R_5$ is —X—Ar—Q—Z, in which X is lower alkylene interrupted by 0, and Ar, Z and Q have meaning as defined above, are prepared by first reacting, e.g. a compound of the formula X

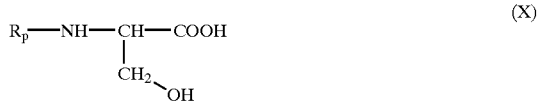
(X)

wherein $R_p$ is an NH protecting group, such as t-butoxycarbonyl (Boc), with e.g. a compound of the formula XI

(XI)

wherein Ar and Q have meaning as defined above, Z being e.g. esterified carboxyl such as trimethylsilyloxyethylcarbonyl, lower alkoxycarbonyl or allyloxycarbonyl, and V is a reactive leaving group such as halo or lower alkylsulfonyloxy. The condensation is carried out in the presence of 2 equivalents of a strong base, e.g. sodium hydride in an anhydrous solvent such as dimethylformamide, to obtain an acid of formula XII

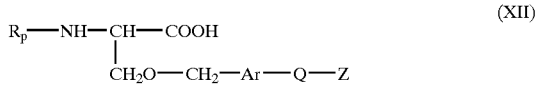

(XII)

wherein $R_p$, Ar, Q and Z have meaning as defined herein. Such is converted to the corresponding compound of formula VI as described above.

The starting amino acids (wherein $R_1$ is hydrogen in formula VII) are either known in the art or are prepared according to methods known in the art.

The condensation according to process (b) is carried out by e.g. coupling the amine of formula VIIIa with triarylbismuth diacetate (*Chem. Rev.* 1989, 89, 1487) or arylboronic acid (*Tetrahedron Let.*, 1998, 39, 2933) catalyzed by cupric acetate, as illustrated below for the preparation of a compound of formula IV.

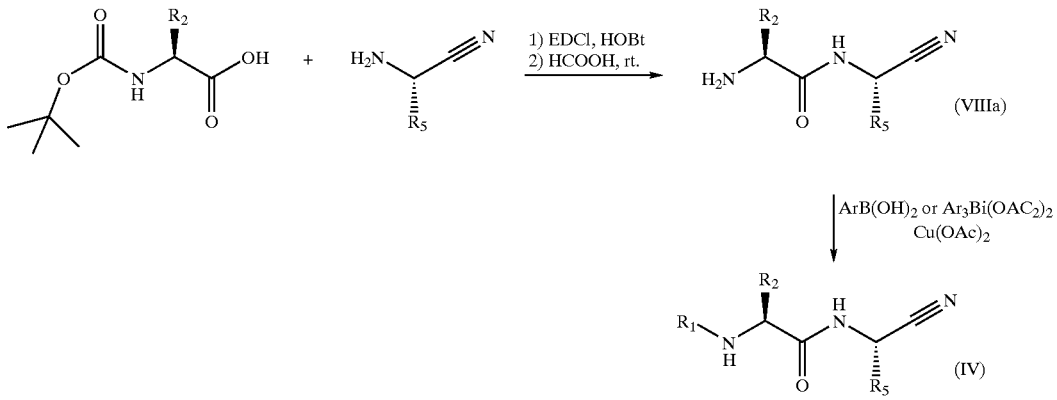

In the above processes, when $R_5$ has a protected carboxylic acid substituent, this group is deprotected in the final step, e.g. using Pd(0) and morpholine if the acid is protected as its allyl ester, or using LiI/pinacolone if the acid is protected as its methyl ester, or using tetrabutyl amonium fluoride in THF, if the protecting group is a trimethylsilylethyl ester. When $R_5$ contains a protected tetrazole substituent, e.g. the cyanoethyl protecting group is removed in the final step using DBU in $CH_2Cl_2$, as illustrated in the examples.

Finally, compounds of the invention are either obtained in the free form, or as a salt thereof if salt forming groups are present.

Any acidic compounds of the invention may be converted into metal salts with pharmaceutically acceptable bases, e.g. an aqueous alkali metal hydroxide, advantageously in the presence of an ethereal or alcoholic solvent, such as a lower alkanol. Resulting salts may be converted into the free compounds by treatment with acids. These or other salts can also be used for purification of the compounds obtained. Ammonium salts are obtained by reaction with the appropriate amine, e.g. diethylamine, and the like.

Compounds of the invention having basic groups can be converted into acid addition salts, especially pharmaceutically acceptable salts. These are formed, for example, with inorganic acids, such as mineral acids, for example sulfuric acid, a phosphoric or hydrohalic acid, or with organic carboxylic acids, such as ($C_1$-$C_4$)alkanecarboxylic acids which, for example, are unsubstituted or substituted by halogen, for example acetic acid, such as saturated or unsaturated dicarboxylic acids, for example oxalic, succinic, maleic or fumaric acid, such as hydroxycarboxylic acids, for example glycolic, lactic, malic, tartaric or citric acid, such as amino acids, for example aspartic or glutamic acid, or with organic sulfonic acids, such as ($C_1$-$C_4$)-alkylsulfonic acids (for example methanesulfonic acid) or arylsulfonic acids which are unsubstituted or substituted (for example by halogen). Preferred are salts formed with hydrochloric acid, methanesulfonic acid and maleic acid.

In view of the close relationship between the free compounds and the compounds in the form of their salts, whenever a compound is referred to in this context, a corresponding salt is also intended, provided such is possible or appropriate under the circumstances.

The compounds, including their salts, can also be obtained in the form of their hydrates, or include other solvents used for their crystallization.

The pharmaceutical compositions according to the invention are those suitable for enteral, such as oral or rectal, transdermal, topical, and parenteral administration to mammals, including man, to inhibit cathepsin activity, and for the treatment of cathepsin dependent disorders, and comprise an effective amount of a pharmacologically active compound of the invention, alone or in combination, with one or more pharmaceutically acceptable carriers.

More particularly, the pharmaceutical compositions comprise an effective cathepsin inhibiting amount of a compound of the invention.

The pharmacologically active compounds of the invention are useful in the manufacture of pharmaceutical compositions comprising an effective amount thereof in conjunction or admixture with excipients or carriers suitable for either enteral or parenteral application. Preferred are tablets and gelatin capsules comprising the active ingredient together with a) diluents, e.g. lactose, dextrose, sucrose, mannitol, sorbitol, cellulose and/or glycine; b) lubricants, e.g. silica, talcum, stearic acid, its magnesium or calcium salt and/or polyethyleneglycol; for tablets also c) binders e.g. magnesium aluminum silicate, starch paste, gelatin, tragacanth, methylcellulose, sodium carboxymethylcellulose and or polyvinylpyrrolidone; if desired d) disintegrants, e.g. starches, agar, alginic acid or its sodium salt, or effervescent mixtures; and/or e) absorbents, colorants, flavors and sweeteners. Injectable compositions are preferably aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1 to 75%, preferably about 1 to 50%, of the active ingredient.

Tablets may be either film coated or enteric coated according to methods known in the art.

Suitable formulations for transdermal application include an effective amount of a compound of the invention with carrier. Advantageous carriers include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

Suitable formulations for topical application, e.g. to the skin and eyes, are preferably aqueous solutions, ointments, creams or gels well-known in the art. Such may contain solubilizers, stabilizers, tonicity enhancing agents, buffers and preservatives.

The pharmaceutical formulations contain an effective cathepsin inhibiting amount of a compound of the invention as defined above, either alone or in combination with another therapeutic agent.

In conjunction with another active ingredient, a compound of the invention may be administered either simultaneously, before or after the other active ingredient, either separately by the same or different route of administration or together in the same pharmaceutical formulation.

The dosage of active compound administered is dependent on the species of warm-blooded animal (mammal), the body weight, age and individual condition, and on the form of administration. A unit dosage for oral administration to a mammal of about 50 to 70 kg may contain between about 10 and 500 mg of the active ingredient.

The present invention also relates to methods of using the compounds of the invention and their pharmaceutically acceptable salts, or pharmaceutical compositions thereof, in mammals to inhibit cathepsins, such as cathepsin B, L and/or S, and for the treatment of cathepsin dependent conditions, such as cathepsin B, L and/or S dependent conditions, described herein, e.g. inflammation, rheumatoid arthritis and osteoarthritis.

Particularly the present invention relates to a method of selectively inhibiting cathepsin activity in a mammal which comprises administering to a mammal in need thereof an effective cathepsin inhibiting amount of a compound of the invention.

More specifically such relates to a method of treating rheumatoid arthritis, osteoarthritis, and inflammation in mammals which comprises administering to a mammal in need thereof a correspondingly effective amount of a compound of the invention.

The following examples are intended to illustrate the invention and are not to be construed as being limitations thereon. Temperatures are given in degrees Centigrade. If not mentioned otherwise, all evaporations are performed under reduced pressure, preferably between about 15 and 100 mm Hg (=20–133 mbar). The structure of final products, intermediates and starting materials is confirmed by standard analytical methods, e.g. microanalysis and spectroscopic characteristics (e.g. MS, IR, NMR). Abbreviations used are those conventional in the art, for example:

AIBN=2,2'-Azobisisobutyronitrile
NBS=N-Bromosuccinimide
TEBA=Triethylbenzylammonium chloride
Boc=t-Butoxycarbonyl
DBU=1,8-Diazabicyclo[5.4.0]undec-7-ene
TPTU=O-(1,2-Dihydro-2-oxo-1-pyridyl)-N,N,N',N'-tetramethyluronium tetrafluoroborate
EDCI=1-(3-Dimethylaminopropyl)-3-ethylcarbodiimide hydrochloride
HOBT=1-Hydroxybenzotriazole hydrate
HOAT=1-Hydroxy-7-azabenzotriazole
NMM=N-Methylmorpholine

EXAMPLE 1

Syntheses of Intermediates (a) (S)-2-Amino-3-[3-(allyloxycarbonyl)-benzyloxy]-propionitrile

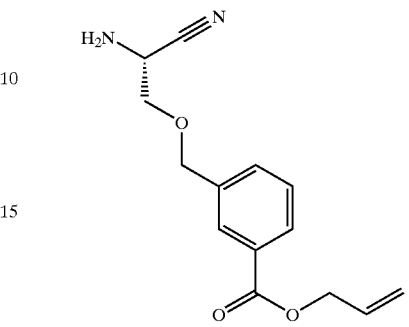

A solution of 3-(chloromethyl)-benzoic acid (50.0 g, 0.293 mol), potassium carbonate (48.61 g, 0.352 mol) and allyl bromide (50.7 mL, 0.586 mol) in acetone (500 mL) is refluxed for 2 hours, after which time the solution is cooled to room temperature and filtered through celite. The filtrate is evaporated and the residue chromatographed (silica, 5% EtOAc/hexane) to yield allyl 3-(chloromethyl)-benzoate as a clear oil.

A solution of allyl 3-(chloromethyl)-benzoate (54.5 g, 0.259 mmol) and sodium iodide (46.56 g, 0.311 mol) in acetone (500 mL) is stirred at room temp. for 6.5 hours, after which time the mixture is filtered. The filtrate is evaporated and the residue is dissolved in diethyl ether (500 mL), then washed with water (1×200 mL), 5% sodium sulfite solution (1×200 mL) and brine (1×200 mL), dried over magnesium sulfate, and evaporated to yield allyl 3-(iodomethyl)-benzoate as a white solid.

Sodium hydride (19.4 g, 60% in mineral oil, 484.4 mmol) is washed with dry hexanes (2×30 mL) to remove the mineral oil and then suspended in anhydrous DMF (330 mL). To this suspension a solution of N-(t-butoxycarbonyl)-L-serine (45.2 g, 220.2 mmol) in DMF (110 mL) at 0° C. is added dropwise with vigorous stirring. The mixture is stirred for an additional 5 minutes at 0° C., and then at room temperature for 30 minutes. The solution is cooled back to 0° C., and a solution of allyl 3-iodomethylbenzoate (66.6 g, 220.2 mmol) in DMF (110 mL) is added dropwise over 15 minutes. The mixture is then warmed to room temperature for 30 minutes. The reaction mixture is poured into ice water (2.2 L) and acidified to pH 2 with 1 N HCl (270 mL). The mixture is extracted with ether (1×600 mL, then 3×300 mL) and the combined ether extracts are then washed with water (5×200 ml) and then dried (MgSO$_4$) and evaporated in vacuo to yield O-[3-(allyloxycarbonyl)-benzyl]-N-(t-butoxycarbonyl)-L-serine as a yellowish oil.

A solution of O-[3-(allyloxycarbonyl)-benzyl]-N-(t-butoxycarbonyl)-L-serine (79.2 g, 209 mmol) and N-methylmorpholine (68.9 mL, 63.4 g, 627 mmol) in CH$_2$Cl$_2$ (800 mL) is cooled to −10° C., and isobutyl chloroformate (32.5 mL, 34.2 g, 251 mmol) is added dropwise over 10 minutes. After stirring for 15 minutes, ammonia gas is bubbled into the solution at a moderately vigorous rate for 15 minutes, at −10° C. The solution is then warmed to room temperature and stirred for 30 minutes. The reaction mixture is cooled to 0° C. and 1 N HCl (800 mL) is added. The organic phase is washed with 1 N HCl (2×700 mL), then washed with saturated NaHCO$_3$ (700 mL), then dried (MgSO$_4$) and evaporated in vacuo to yield O-[3-

(allyloxycarbonyl)-benzyl]-N-(t-butoxycarbonyl)-L-serinamide as a thick oil.

To dry DMF (50 mL) at 0° C. is added oxalyl chloride (9.55 g, 6.56 mL, 75.24 mmol) slowly, via syringe. The mixture is then stirred at 0° C. for 5 minutes after which time pyridine (12.2 mL, 150.48 mmol) is added in one portion, followed by O-[3-(allyloxycarbonyl)-benzyl]-N-(t-butoxycarbonyl)-L-serinamide (14.22 g, 37.62 mmol) in DMF (50 mL). The mixture is stirred at 0° C. for 45 minutes then diluted with ethyl acetate (600 mL), washed with sat'd aqueous LiCl (3×600 ml), and dried over $MgSO_4$. Evaporation of solvent, followed by chromatography (silica, 35% EtOAc/hexane) yields (S)-2-t-butoxycarbonylamino-3-[(3-allyloxycarbonyl)-benzyloxy]-propionitrile, as a clear oil.

(S)-2-t-Butoxycarbonyl amino-3-[(3-allyloxycarbonyl)-benzyloxyl-propionitrile (11.78 g, 32.72 mmol) in formic acid (125 mL) is stirred at room temperature for 6 hours, after which time the formic acid is evaporated at 25° C. The residue is then dissolved in water (50 mL), basified with sat'd aqueous $NaHCO_3$, and extracted with ethyl acetate (3×150 mL). The combined organic layers are then washed with water (50 mL), brine (50 mL), dried ($MgSO_4$) and evaporated to yield (S)-2-amino-3-[3-(allyloxycarbonyl)-benzyloxy]-propionitrile, as a light yellow oil, which is utilized without further purification.

(b) (S)-2-Amino-3-[(3-allyloxycarbonyl-4-fluoro)-benzyloxy]-propionitrile

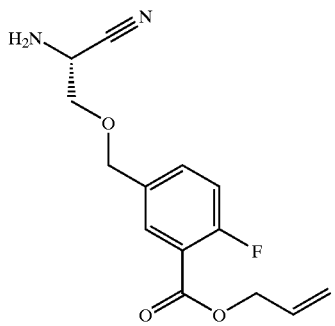

To a solution of 2-fluoro-5-methylbenzoic acid (20.0 g, 0.13 mol) in MeOH (100 mL) is added thionyl chloride (1.9 mL, 26.0 mmol) dropwise, via syringe, and the solution is refluxed overnight. After cooling, the solvent is evaporated, and the residue is taken up in ethyl acetate (200 mL), extracted with sat'd aq. $NaHCO_3$ (50 mL), brine (50 mL), water (50 mL), dried ($MgSO_4$), and chromatographed (silica, 5% EtOAc/hexane) to yield methyl 2-fluoro-5-methylbenzoate, as a clear oil.

To a solution of methyl 2-fluoro-5-methylbenzoate (17.16 g, 102.1 mmol) in $CCl_4$(250 mL) is added NBS (18.2 g, 102.1 mmol) and AIBN (0.83 g, 5.1 mmol), and the resulting solution is refluxed for 3 hours. After cooling, the mixture is filtered through celite, evaporated, and chromatographed (silica, 5 to 15% EtOAc/hexane) to yield methyl 5-bromomethyl-2-fluorobenzoate, as a white solid.

To a solution of methyl 5-bromomethyl-2-fluorobenzoate (12.49 g, 50.6 mmol) in methylene chloride (150 mL) at 0° C. is added $BBr_3$ (5.26 mL, 55.62 mmol) slowly, via syringe. The solution is then warmed to room temperature over 2.5 hours, and then is cooled back down to 0° C., and allyl alcohol (103 mL, 1.52 mol) is added dropwise. The solution is then stirred overnight, after which time it is diluted with $CH_2Cl_2$ (250 mL), then washed with sat'd aq. $NaHCO_3$ (2×300 mL), brine (150 ml), and dried over $MgSO_4$. Evaporation of solvent yields allyl 5-bromomethyl-2-fluorobenzoate.

Allyl 5-bromomethyl-2-fluorobenzoate is then reacted as described under (a) to prepare the target intermediate, (S)-2-amino-3-[(3-allyloxycarbonyl-4-fluoro)-benzyloxy]-propionitrile.

(c) (S)-2-Amino-3-(5-allyloxycarbonyl-furan-2-yl-methoxy)-propionitrile

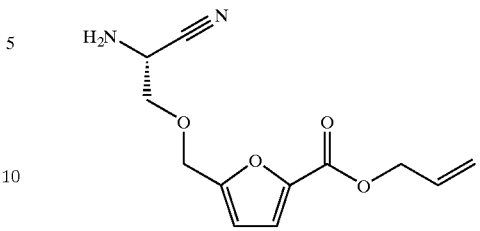

To a solution of 5-methylfurfural (18 mL, 0.18 mmol) in $CCl_4$ (400 mL) is added pulverized N-bromosuccinimide (71.1 g, 0.40 mmol), and the solution is subjected to sun lamp irradiation. After 15 minutes, the solution begins to reflux vigorously, and then settles down after another 2–3 minutes. After an additional 10 minutes, the dark mixture is cooled to room temperature, and allyl alcohol (200 mL) is added. After 2 hours, the solution is evaporated, and the residue is diluted with $Et_2O$, and washed with saturated $NaHCO_3$ (100 mL), water (100 mL) and brine (100 mL), dried over $MgSO_4$ and evaporated. The residue is chromatographed (silica, 4% EtOAc/hexane) to yield allyl 5-(bromomethyl)-2-furoate, as a yellow oil.

Allyl 5-(bromomethyl)-2-furoate is reacted as previously described to yield (S)-2-Amino-3-(5-allyloxycarbonyl-furan-2-yl-methoxy)-propionitrile.

(d) (S)-2-Amino-5-[3-(methoxycarbonyl)-phenyl]-valeronitrile

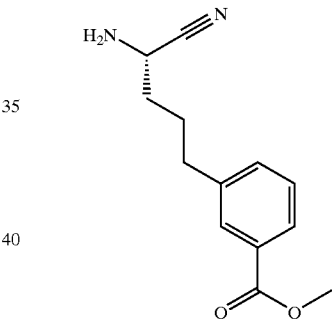

To a solution of (S)-N-(t-butoxycarbonyl)-propargylglycine (2.44 g, 11.45 mmol) in $CH_2Cl_2$ (50 mL) is added N-methylmorpholine (3.78 mL, 34.4 mmol) in one portion. The solution is then cooled to −10° C., and isobutyl chloroformate is added dropwise over 5 minutes. After stirring for 15 minutes, ammonia gas is bubbled into the reaction mixture at a moderately vigorous rate for 15 minutes. The resulting milky suspension is then warmed to room temperature over 2 hours, and the mixture is washed with 1 N HCl (2×25 mL), aqueous $NaHCO_3$ (25 mL) and brine (25 mL), and then dried over $MgSO_4$. Evaporation of solvent, followed by chromatography (silica, 65% EtOAc/hexane) yields
(S)-N-(t-butoxycarbonyl)-propargylglycineamide, as a Clear Oil.

A solution of (S)-N-(t-butoxycarbonyl)-propargylglycineamide (1.15 g, 5.33 mmol), methyl 3-bromobenzoate (1.15 g, 5.33 mmol), and Cu(I)I (0.041 g, 0.214 mmol) in triethylamine (25 mL) is deoxygenated with bubbling $N_2$ for 2–3 minutes. Bis(triphenylphosphine) palladium dichloride (0.075 g, 0.11 mmol) is then added in one portion, and the mixture is refluxed for 3 hours, after which time solvent is evaporated. The residue is taken up in EtOAc (10 ml), then washed with 1 N HCl (40 mL) and brine (30 mL), and then dried over MgSO$_4$. The residue is chromatographed (silica, 80% EtOAc/hexane) to yield (S)-2-(t-butoxycarbonylamino)-5-(3-carbomethoxyphenyl)-4-pentynoic acid amide, as a light yellow solid.

To a solution of (S)-2-(t-butoxycarbonylamino)-5-(3-carbomethoxyphenyl)-4-pentynoic acid amide (1.11 g, 3.22 mmol) in 1:1 ethanol/THF (50 mL) is added 10% Pd/C (0.5 g), and the mixture is hydrogenated at 1 atm. for 1.5 hours. The mixture is filtered through celite, and evaporated to yield (S)-2-(t-butoxycarbonylamino)-4-(3-carbomethoxyphenyl)-pentanamide, as a clear oil.

(S)-2-Butoxycarbonylamino-4-(3-carbomethoxyphenyl)-pentanamide is reacted as previously described to yield (S)-2-amino-5-(3-methoxycarbonylphenyl)-valeronitrile.

(e) (S)-2-amino-3-[3-[1-(2-cyanoethyl)-5-tetrazolyl]-benzyloxy]-propionitrile

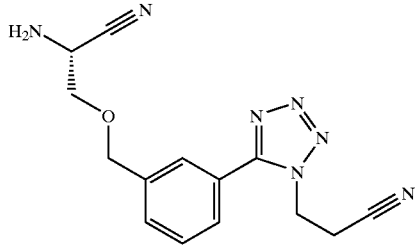

To a solution of (S)-2-t-butoxycarbonylamino-3-(3-allyloxycarbonylbenzyloxy)-propionitrile (8.0 g, 22.22 mmol) in THF (100 mL) is added morpholine (19.4 mL, 222 mmol). After deoxygenation with bubbling nitrogen (2 min.), Pd(PPh$_3$)$_4$ (1.28 g, 1.11 mmol) is added in one portion, and the solution is stirred 1 h. Solvent is evaporated, the residue is taken up in EtOAc (250 mL), and washed with 1 N HCl (250 mL), brine (100 mL), dried (MgSO$_4$), evaporated, and the residue chromatographed (silica, 2% methanol, CH$_2$Cl$_2$) to yield (S)-2-t-butoxycarbonylamino-3-(3-carboxybenzyloxy)-propionitrile, as a light yellow oil.

To a solution of (S)-2-t-butoxycarbonylamino-3-(3-carboxybenzyloxy)-propionitrile (6.5 g, 20.31 mmol) in CH$_2$Cl$_2$ (150 mL) is added N-methylmorpholine (6.7 mL, 60.9 mmol), followed by 3-aminopropionitrile (1.5 mL, 20.3 mmol), HOAt (3.04 g, 22.34 mmol) and EDCI (5.84 g, 30.47 mmol), and the solution is stirred overnight at room temp. The solution is then washed with 1 N HCl (200 mL), sat'd NaHCO$_3$ (200 mL), brine (100 mL), dried (MgSO$_4$), evaporated and chromatographed (silica, 65% EtOAc/hexane) to yield yield (S)-2-t-butoxycarbonylamino-3-[3-(2-cyanoethylaminocarbonyl)-benzyloxyl-propionitrile, as a thick brown oil.

To a solution of (S)-2-t-butoxycarbonylamino-3-[3-(2-cyanoethylaminocarbonyl)-benzyloxy]-propionitrile (3.8 g, 10.2 mmol) and triphenylphosphine (6.7 g, 25.5 mmol) in acetonitrile (75 mL) at 0° C. is added diisopropyl azodicarboxylate (5.0 mL, 25.5 mmol) and trimethylsilyl azide (3.73 mL, 28.1 mmol) dropwise, simultaneously, via syringe. The solution is then stirred at room temp. for 0.5 h, and then heated to 30° C. overnight. After solvent evaporation, the residue is taken up in EtOAc (150 mL), and then poured onto an ice—sat'd NaHCO$_3$ mixture (150 mL), and extracted. The organic phase is washed with brine (100 mL), dried (MgSO$_4$), evaporated and chromatographed (silica, 65% EtOAc/hexane) to yield (S)-2-t-butoxycarbonylamino-3-{3-[1-(2-cyanoethyl)-5-tetrazolyl]-benzyloxy}-propionitrile, as a light yellow oil.

A solution of (S)-2-t-butoxycarbonylamino-3-{3-[1-(2-cyanoethyl)-5-tetrazolyl]-benzyloxy}-propionitrile (3.49 g, 8.8 mmol) in formic acid (22 mL) is stirred at room temp. for 6 h., after which time the formic acid is evaporated at 25° C. The residue is then dissolved in water (50 mL), basified with sat'd aqueous NaHCO$_3$, and extracted with ethyl acetate (3×150 mL). The combined organic layers are then washed with water (50 mL), brine (50 mL), dried (MgSO$_4$) and evaporated to yield (S)-2-amino-3-{3-[1-(2-cyanoethyl)-5-tetrazolyl]-benzyloxy}-propionitrile, as a light yellow oil, which is utilized without further purification.

(f) (S)-2-Amino-3-[3-[(2-trimethylsilylethoxy)-carbonyl]-4-fluorobenzyloxy]-propionitrile

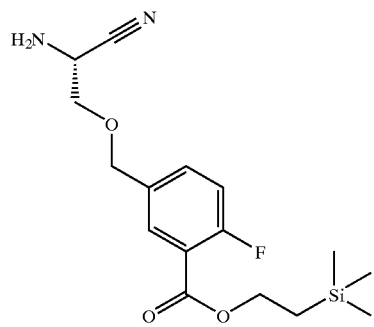

A mixture of 2-fluoro-5-methylbenzoic acid (41.05 g, 0.266 mol) in thionyl chloride (200 mL) is refluxed for 45 min., during which time it becomes homogeneous. After cooling, the thionyl chloride is evaporated to yield 2-fluoro-5-methylbenzoyl chloride, as a yellow liquid, which is dissolved in CH$_2$Cl$_2$ (500 mL), and cooled to 0° C. To this solution is added 2-(trimethylsilyl)-ethanol (48.65 mL, 40.14 g, 0.34 mol), followed by triethylamine (85.86 g, 118.3 mL, 0.85 mol), and the solution is warmed to room temp. over 1 h. The solution is then washed with 1 N HCl (2×500 mL), water (1×250 mL) and brine (1×100 mL), dried (MgSO$_4$), evaporated and chromatographed (silica, 5% EtOAc/hexane) to yield (2-trimethylsilyl)-ethyl 2-fluoro-5-methylbenzoate, as a yellow oil.

To a solution of (2-trimethylsilyl)-ethyl 2-fluoro-5-methylbenzoate (55.46 g, 218 mmol) in CCl$_4$ (400 mL) is added NBS (38.86 g, 218 mmol) and AIBN (0.18 g, 1.1 mmol), and the resulting solution is exposed to sunlamp irradiation for 1.25 h. After cooling, the mixture is filtered through celite and evaporated to yield (2-trimethylsilyl)-ethyl 5-bromomethyl-2-fluororobenzoate, along with small amounts of starting material and dibromomethyl product. (2-Trimethylsilyl)-ethyl 2-bromomethyl-5-fluororobenzoate is then reacted as described under (a) to prepare the target intermediate, (S)-2-Amino-3-[3-[(2-trimethylsilylethoxy)-carbonyl]-4-fluorobenzyloxy]-propionitrile (g) (S)-6-[1-carboxy-2-(3-methylphenyl)-ethylamino]-phthalide

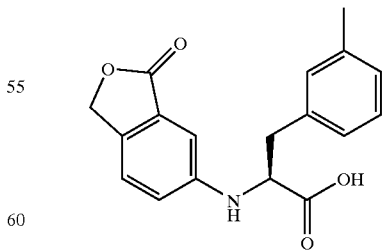

A solution of 6-iodophthalide (1.0 g, 3.85 mmol), (S)-3-methylphenylalanine.HCl (0.83 g, 3.85 mmol) K$_2$CO$_3$ (0.53 g, 3.85 mmol), CuI (73 mg, 0.38 mmol), TEBA (0.32 g, 1.3 mmol), tri-o-tolylphosphine (0.23 g, 0.77 mmol), Pd(OAc)$_2$ (86 mg, 0.38 mmol), triethylamine (2.14 mL, 15.38 mmol)

and water (1.2 mL) in DMF (12 mL) is heated to 100° C. for 12 h. After cooling, the solution is diluted with EtOAc, and washed with 1 N HCl (100 mL), sat'd LiCl (50 mL) and water (100 mL), evaporated and chromatographed (2% MeOH/CH$_2$Cl$_2$, 0 to 0.05% acetic acid) to yield (S)-6-[(1-carboxy-2-(3-methylphenyl)-ethylamino]-phthalide, as a light brown foam.

Other N-arylphenylalanines are similarly prepared.

(h) (S)-2-(3-methoxycarbonylphenylamino)-3-(3-methylphenyl)-propionic Acid

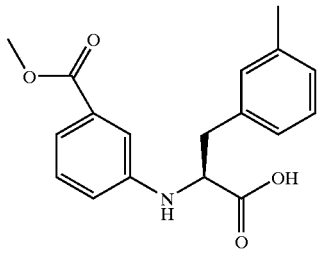

To a solution of D-3-methylphenylalanine.HCl (5.5 g, 25.5 mmol) and acetic acid (13.0 mL) in 0.04 M aqueous sodium acetate (750 mL) is added a solution of sodium nitrite (5.28 g, 76.5 mmol) in water (12.5 mL) dropwise, over 30 min, and the solution is allowed to stir for 3 h. This solution is then saturated with NaCl, and extracted with EtOAc (3×150 mL). The combined organic layers are washed with brine (3×150 mL), dried (MgSO$_4$) and evaporated to yield (R)-2-hydroxy-3-(3-methylphenyl)-propionic acid.

A solution of (R)-2-hydroxy-3-(3-methylphenyl)-propionic acid (6.3 g, 35.0 mmol), benzyl bromide (5.4 mL, 45.5 mmol) and triethylamine (7.31 mL, 52.4 mmol) in EtOAc (100 mL) is refluxed for 6 hours. After cooling, the solution is washed with 1 N HCl (150 mL), water (200 mL), sat'd NaHCO$_3$ (200 mL) and brine (300 mL), dried (MgSO$_4$), evaporated and chromatographed (silica, 10% EtOAc/hexane) to yield benzyl (R)-2-hydroxy-3-(3-methylphenyl)-propionate, as a clear oil.

To a solution of pyridine (0.78 mL, 9.7 mmol) in CH$_2$Cl$_2$ (50 mL) at −10° C. is added triflic anhydride (1.68 mL, 10.0 mmol) over 15 min. A solution of benzyl (R)-2-hydroxy-3-(3-methylphenyl)-propionate (1.5 g, 5.55 mmol) in CH$_2$Cl$_2$ (15 mL) is then added dropwise over 30 min., and the mixture is warmed to room temp. over 1 h. The solution is diluted with CH$_2$Cl$_2$ (100 mL), washed with water (2×100 mL) and brine (100 mL), dried (MgSO$_4$), and evaporated to yield benzyl (R)-2-trifluoromethanesulfonyloxy-3-(3-methylphenyl)-propionate as a yellowish oil.

A solution of benzyl (R)-2-trifluoromethanesulfonyloxy-3-(3-methylphenyl)-propionate (0.59 g, 1.47 mmol) and methyl 3-aminobenzoate (0.44 g, 2.94 mmol) in CH$_2$Cl$_2$ (20 mL) is stirred overnight at room temp for 2 days. Solvent is evaporated, and the residue is chromatographed (silica, 33% CH$_2$Cl$_2$/hexane) to yield benzyl (S)-2-(3-methoxycarbonylphenylamino)-3-(3-methylphenyl)-propionate, as a clear oil.

A mixture of benzyl (S)-2-(3-methoxycarbonylphenylamino)-3-(3-methylphenyl)-propionate (0.25 g, 0.62 mmol) and 10% Pd/C (0.25 g) in EtOH (25 mL) is hydrogenated at 1 atm for 1 h. The mixture is filtered through celite and evaporated to yield (S)-2-(3-methoxycarbonylphenylamino)-3-(3-methylphenyl)-propionic acid, as a grey oil.

(i) (S)$_2$-(tert-Butoxycarbonylamino)-3-(5-methyl-furan-2-yl)-propionic Acid

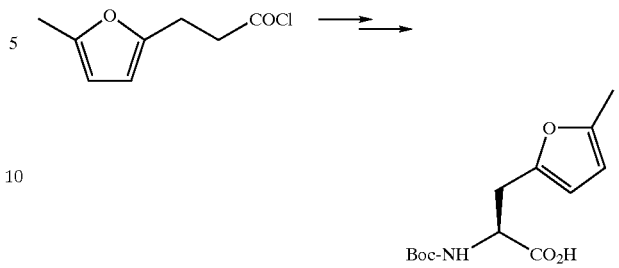

3-(5-Methyl-furan-2-yl)-propionyl chloride (H. Kotsuki et al., *Bull. Chem. Soc. Jpn.*, 1984, 57, 3339) is converted to (S) 2-(tert-butoxycarbonylamino)-3-(5-methyl-furan-2-yl)-propionic acid according to the Evans amino acid protocol (*J. Am. Chem. Soc.* 1990, 112, 4011).

(j) (S)-2-[1-Carboxy-2-(3-methylphenyl)]-ethylaminobenzoxazole

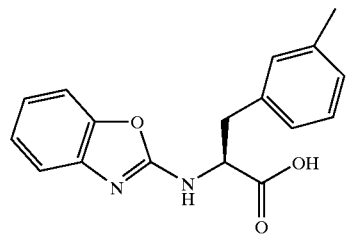

To a solution of 2-phenoxybenzoxazole (0.65 g, 3.11 mmol) is added (S)-3-methylphenylalanine methyl ester (1.8 g, 9.33 mmol), and the solution is heated at 45° C. for 6 h. Chromatography (10% EtOAc/hexane, SiO$_2$) yields (S)-2-[1-methoxycarbonyl-2-(3-methylphenyl)]-ethylaminobenzoxazole, as a clear oil.

To a solution of (S)-2-[1-methoxycarbonyl-2-(3-methylphenyl)]-ethylaminobenzoxazole (400 mg, 1.1 mmol) in 2:1:1 THF/MeOH/water (24 mL) is added LiOH.H$_2$O, and the solution is stirred for 1.5 h. Solvent is evaporated, and the residue is dissolved in diethyl ether (50 mL) and washed with water (50 mL). The aqueous layer is then acidified with 1 N HCl (pH 2) and extracted with EtOAc (3×30 mL). The organic layer is washed with brine (20 mL) dried (MgSO$_4$) and evaporated to yield (S)-2-(1-carboxy-2-(3-methylphenyl)]-ethylaminobenzoxazole as a clear oil.

(k) (S)-2-Amino-3-(6-allyloxycarbonyl-2-picolyloxy)-propionitrile

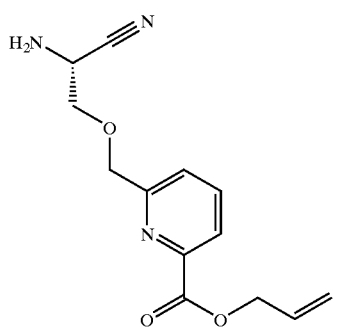

A stirred solution of 2,6-pyridinedicarboxylic acid chloride (3.51 g, 0.0172 mol) in 100 mL of THF is cooled to 0°

C. then 12 mL (0.172 mol) of allyl alcohol and 7.1 mL (0.069 mol) of NMM are added simultaneously. The reaction is allowed to stir at 25° C. for 2 h, and then diluted with 100 mL of Et$_2$O and washed with 100 mL water. The aqueous phase is extracted with Et$_2$O (2×50 mL) and the combined extracts are washed with brine and dried with MgSO$_4$. Filtration and concentration yields diallyl 2,6-pyridinedicarboxylate as a clear oil which is used without further purificiation.

A mixture of diallyl 2,6-pyridinedicarboxylate (17.1 g, 0.069 mol) in 150 mL of THF, and 150 mL of allyl alcohol is stirred at room temperature. Sodium borohydride (1.32 g, 0.035 mol) is added in several portions over 10 minutes, and the reaction is allowed to stir at room temperature for 15 h. The reaction is quenched by slow addition of 30 mL of water, followed by 30 mL of 1.0 N HCl. The mixture is poured into a separatory funnel containing 100 mL of 5% ammonium hydroxide and extracted with 1:1 ethyl acetate-diethyl ether (3×100 mL). The combined organic fractions are washed with brine, dried with MgSO$_4$, filtered, and concentrated in vacuo to give a yellow oil which solidified on standing. Trituration with 1:1 diethyl ether/hexane affords allyl 6-(hydroxymethyl)pyridine-2-carboxylate as a white crystalline solid.

A solution of allyl 6-(hydroxymethyl)pyridine-2-carboxylate (1.0 g, 5.17 mmol) in 20 mL of CH$_2$Cl$_2$ is cooled to 0° C. under argon and 3.43 g (10.3 mmol) of CBr$_4$ is added. Then, 1.5 g (5.69 mmol) of triphenyl phosphine is added in several portions over 20 min. The reaction is allowed to stir at 0° C. for 3 h and is then concentrated in vacuo and applied to a short silica gel column. Elution with 1:1 EtOAc-hexane yields allyl 6-(bromomethyl)pyridine-2-carboxylate as an oil.

Allyl 6-(bromomethyl)pyridine-2-carboxylate is reacted as previously described to yield (S)-2-amino-3-(6-allyloxycarbonyl-2-picolyloxy)-propionitrile using the procedure described in the first synthetic example.

(1) (S)-2-Amino-3-(2-allyloxycarbonyl-4-picolyloxy) propionitrile

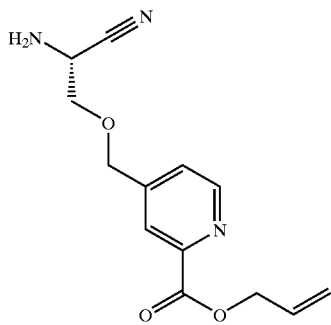

Solid sodium hydroxide (22.2 g, 0.554 mol) is added to a stirred solution of 2-cyano-4-[{(tert-butyldimethylsilyl)oxy}methyl]pyridine in 300 mL EtOH and 50 mL water. The reaction mixture is then heated at reflux for 15 h. After cooling to room temperature, the solution is adjusted to pH 1–2 by addition of 6N HCl, then the mixture is concentrated to dryness in vacuo. The solid residue is washed with ethanol, then dried in vacuo to give crude 4-(hydroxymethyl)pyridine-2-carboxylic acid hydrochloride as a tan solid. The crude salt is disolved in 280 mL DMF, then 18.2 g (0.131 mol) of potassium carbonate is added, followed by 4.8 mL (0.0554 mol) of allyl bromide. The resulting mixture is allowed to stir at room temperature for 48 h, then concentrated under high vacuum. This residue is taken up in ethyl acetate and washed three times with saturated LiCl and finally with brine. The aqueous washings are combined and extracted with CH$_2$Cl$_2$. The combined organic layers are dried over Na$_2$SO$_4$ and concentrated. Silica gel chromatography eluting with 97:3 CH$_2$Cl$_2$-MeOH gives allyl 4-(hydroxymethyl)pyridine-2-carboxylate as a dark oil.

Allyl 4-(hydroxymethyl)pyridine-2-carboxylate is converted to (S)-2-amino-3-(2-allyloxycarbonyl-4-picolyloxy)-propionitrile as described above.

EXAMPLE 2

N-[2-[3-(Allyloxycarbonyl)-benzyloxy]-1(S)-cyanoethyl]-3-methyl-L-phenylalaninamide

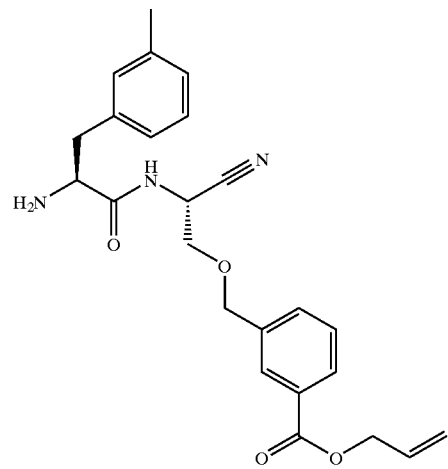

To a solution of (S)-boc-(3-methylphenyl)-alanine (3.22 g, 11.54 mmol) and (S)-2-amino-3-[(3-allyloxycarbonyl)-benzyloxy]-propionitrile (3.0 g, 11.54 mmol) in CH$_2$Cl$_2$ (100 mL) is added N-methylmorpholine 3.8 mL, 34.6 mmol), followed by HOAt (1.88 g, 13.8 mmol) and EDCI (3.32 g, 17.3 mmol), and the solution is stirred overnight at room temp. The solution is then washed with 1 N HCl (100 mL), sat'd NaHCO$_3$ (100 mL), brine (100 mL), dried (MgSO$_4$), evaporated and chromatographed (silica, 25% EtOAc/hexane) to yield yield N-[2-[3-(allyloxycarbonyl)-benzyloxy]-1(S)-cyanoethyl]-3-methyl-Nα-(t-butoxycarbonyl)-L-phenylalaninamide, as a white solid.

N-[2-[3-(allyloxycarbonyl)-benzyloxy]-1(S)-cyanoethyl]-3-methyl-Nα-(t-butoxycarbonyl)-L-phenylalaninamide (4.36 g, 8.37 mmol) in formic acid (47 mL) is stirred at room temp. for 6 h, after which time the formic acid is evaporated at 25° C. The residue is then dissolved in water (50 mL), basified with sat'd aqueous NaHCO$_3$, and extracted with ethyl acetate (3×50 mL). The combined organic layers are then washed with water (50 mL), brine (50 mL), dried (MgSO$_4$) and evaporated to yield N-[2-[3-(allyloxycarbonyl)-benzyloxy]-1(S)-cyanoethyl]-3-methyl-L-phenylalaninamide, as a clear oil, which is utilized without further purification.

EXAMPLE 3

N-[2-[3-(allyloxycarbonyl)-benzyloxy]-1(S)-cyanoethyl]-3-methyl-Nα-(3-oxo-1,3-dihydroisobenzofuran-5-yl)-L-phenylalaninamide

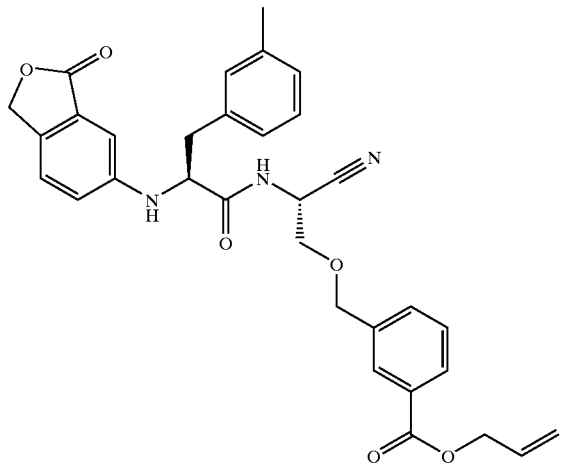

To a solution of (S)-6-[1-carboxy-2-(3-methylphenyl)-ethylamino]-phthalide (0.47 g, 1.5 mmol) and (S)-2-amino-3-[(3-allyloxycarbonyl)-benzyloxy]-propionitrile (0.39 g, 1.5 mmol) in CH$_2$Cl$_2$ (50 mL) is added N-methylmorpholine (0.50 mL, 4.51 mmol), followed HOBt (0.25 g, 1.65 mmol)) and EDCI (0.43 g, 2.25 mmol), and the solution is stirred overnight at room temp. The solution is then washed with 1 N HCl (50 mL), sat'd NaHCO$_3$ (50 mL), brine (50 mL), dried (MgSO$_4$), evaporated and chromatographed (silica, 30% to 45% EtOAc/hexane) to yield N-[2-[3-(allyloxycarbonyl)-benzyloxy]-1(S)-cyanoethyl]-3-methyl-Nα-(3-oxo-1,3-dihydroisobenzofuran-5-yl)-L-phenylalaninamide, as a light yellow oil.

EXAMPLE 4

N-[2-[3-(allyloxycarbonyl)-benzyloxy]-1(S)-cyanoethyl]-3-methyl-Nα-phenyl-L-phenylalaninamide

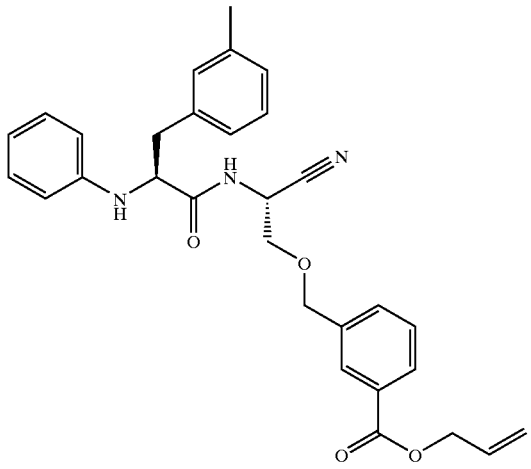

To a solution of N-[2-[3-(allyloxycarbonyl)-benzyloxy]-1(S)-cyanoethyl]-3-methyl-L-phenylalaninamide (Example 2, 13.43 g, 31.9 mmol) in CH$_2$Cl$_2$ (1.2 L) is added triphenylbismuth diacetate (19.58 g, 35.09 mmol) and cupric acetate (0.58 g, 3.19 mmol), and the solution is stirred at room temp. overnight. The solution is then filtered through celite to remove the white precipitate which is formed, and evaporated. The residue is chromatographed (30% EtOAc/hexane) to yield N-[2-[(3-(allyloxycarbonyl)-benzyloxyl-1(S)-cyanoethyl]-3-methyl-Nα-phenyl-L-phenylalaninamide.

EXAMPLE 5

N-[2-[3-(Allyloxycarbonyl)-benzyloxyl-1(S)-cyanoethyl]-3-methyl-Nα-(4-fluorophenyl)-L-phenylalaninam

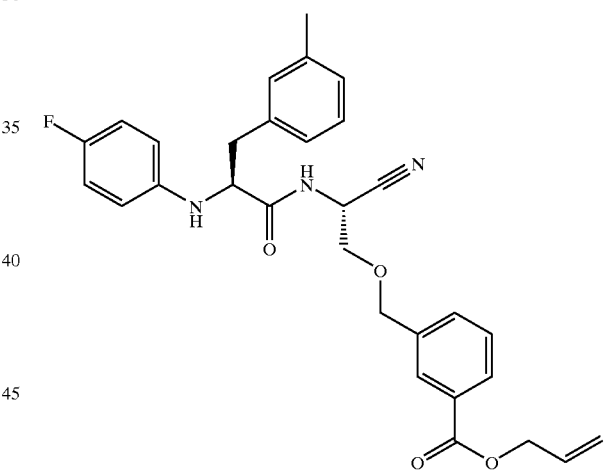

To a solution of N-[2-[3-(allyloxycarbonyl)-benzyloxy]-1(S)-cyanoethyl]-3-methyl-L-phenylalaninamide (0.6 g, 1.42 mmol) in CH$_2$Cl$_2$ (15 mL) is added 4-fluorophenylboronic acid (0.398 g, 2.85 mmol), cupric acetate (0.26 g, 1.4 mmol) and pyridine (0.23 mL, 2.85 mmol), and the dark blue solution is stirred overnight at room temp. The solution is then diluted with CH$_2$Cl$_2$ (35 mL), and washed with 1 N HCl (50 mL) and brine (50 mL), then dried (MgSO$_4$), evaporated and chromatographed (silica, 30% EtOAc/hexane) to yield N-[2-[3-(allyloxycarbonyl)-benzyloxy]-1(S)-cyanoethyl]-3-methyl-Nα-(4-fluorophenyl)-L-phenylalaninamide, as a clear oil.

EXAMPLE 6

N-[2-(3–Carboxy-benzyloxy)-1(S)-cyanoethyl]-3-methyl-Nα-phenyl-L-phenylalaninamide

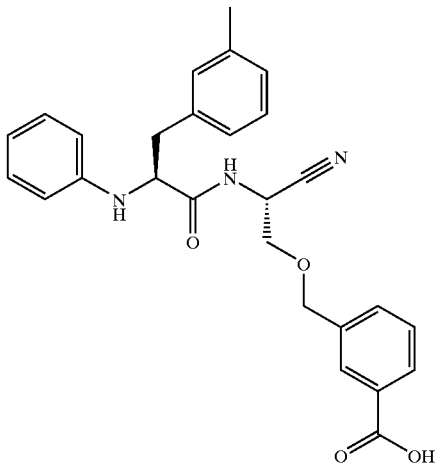

To a solution of N-[2-[3-(allyloxycarbonyl)-benzyloxy]-1(S)-cyanoethyl]-3-methyl-Nα-phenyl-L-phenylalaninamide (12.48 g, 25.11 mmol) in THF (500 mL), is added morpholine (21.9 mL, 251 mmol), and the solution is deoxygenated with bubbling N₂ for 5 min. Pd(PPh₃)₄ is then added in one portion, and the solution is stirred at room temp. for 10 min. Solvent is evaporated, and the residue is dissolved in EtOAc (500 mL), and washed with 1 N HCl (500 mL), brine (200 mL), dried (MgSO₄), evaporated and chromatographed (2%–10% MeOH/CH₂Cl₂) to yield N-[2-(3-carboxy-benzyloxy)-1(S)-cyanoethyl]-3-methyl-Nα-phenyl-L-phenylalaninamide, as a white solid; m.p. 135–137°.

EXAMPLE 7

N-(5-(3-carboxyphenyl)-1(S)-cyanopentyl]-3-methyl-Nα-(3-oxo-1,3-dihydroisobenzofuran-5-yl)-L-phenylalaninamide

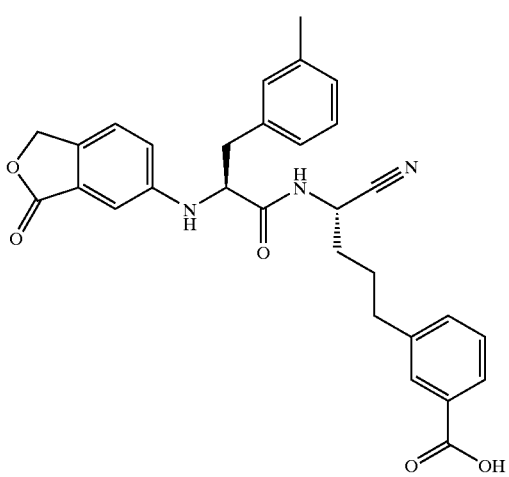

A solution of N-(5-(3-methoxycarbonylphenyl)-1(S)-cyanopentyl]-3-methyl-Nα-(3-oxo-1,3-dihydro-isobenzofuran-5-yl)-L-phenylalaninamide (0.354 g, 0.67 mmol) in pinacolone (15 mL) is deoxygenated with bubbling N₂ for 5 min., after which time LiI (0.90 g, 6.74 mmol) is added in one portion. The solution is then heated to 100° C. for 28 h. After cooling, it is diluted with EtOAc (100 mL), and washed with 1 N HCl (100 mL), and brine (50 mL), then dried (MgSO₄), evaporated and chromatographed (2% MeOH/CH₂Cl₂, 0% to 0.05% acetic acid) to yield N-(5-(3-carboxyphenyl)-1(S)-cyanopentyl]-3-methyl-Nα-(3-oxo-1,3-dihydro-isobenzofuran-5-yl)-L-phenylalaninamide, as a light yellow solid; m.p. 91–94° C.

EXAMPLE 8

N-[2-[3-(5-Tetrazolyl)-benzyloxy]-1(S)-cyanoethyl]-3-methyl-Nα-phenyl-phenylalaninamide

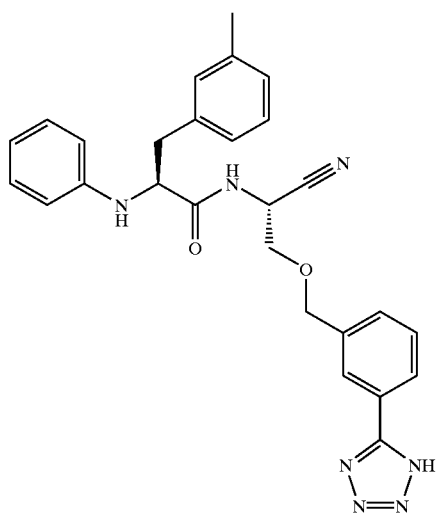

To a solution of N-[2-[3-(1-(2-cyanoethyl)-5-tetrazolyl)-benzyloxy]-1(S)-cyanoethyl]-3-methyl-Nα-phenyl-L-phenylalaninamide (prepared according to examples 1(g) and 7 using intermediate of Example 1(e)), 160 mg, 0.30 mmol) in CH₂Cl₂ (10 mL) is added DBU (0.22 mL, 1.5 mmol) in one portion, and the solution is stirred at room temp. for 2 h., after which time the solution is washed with 1 N HCl (30 mL), brine (30 mL), dried (MgSO₄), evaporated, and chromatographed (2% MeOH/CH₂Cl₂, 0 to 0.05% acetic acid) to yield N-[2-[3-(5-tetrazolyl)-benzyloxy]-1(S)-cyanoethyl]-3-methyl-Nα-phenyl-phenylalaninamide, as an off-white solid; m.p. 120–122° C.

EXAMPLE 9

N-[2-[(3–Carboxy)-4-fluoro-benzyloxy]-1(S)-cyanoethyl]-3-methyl-Nα-phenyl-3-methyl-L-phenylalaninamide

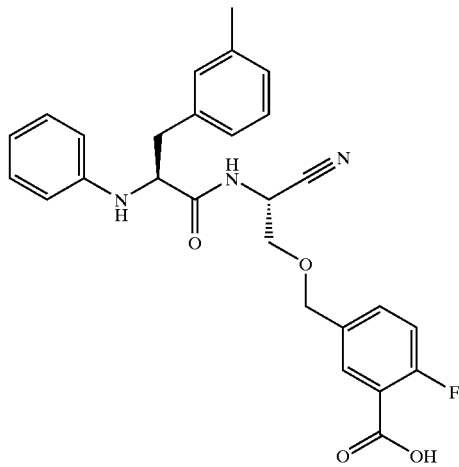

Condensation according to Example 7 of (S)-2-amino-3-[3-[(2-trimethylsilylethoxy)-carbonyl]-4-fluoro-benzyloxy] propionitrile (see Example 1f) and N-phenyl-3-methyl-L-phenylalanine (prepared according to Example 1g) yields N-[2-[(3-((2-trimethylsilyl)-ethoxycarbonyl)-4-fluoro-benzyloxy]-1(S)-cyanoethyl]-3-methyl-Nα-phenyl-L-phenylalaninamide.

A solution of N-[2-[(3-((2-trimethylsilyl)-ethoxycarbonyl)-4-fluoro-benzyloxy]-1(S)-cyanoethyl]-3-methyl-Nα-phenyl-L-phenylalaninamide (17.44 g, 30.33 mmol) in THF (200 mL) is cooled to 0° C., and tetrabutylammonium fluoride (1 N in THF, 61 mL, 61 mmol) is added over 10 min. The solution is then warmed to room temp. over 1.5 h. After this time, it is diluted with diethyl ether (1 L), and washed with 1 N HCl (500 mL), water (500 mL) and brine (200 mL), dried (MgSO$_4$), evaporated, chromatographed (2%–10% MeOH/CH$_2$Cl$_2$) and crystallized from diethyl ether to yield N-[2-[(3-carboxy)-4-fluoro-benzyloxy]-1(S)-cyanoethyl]-3-methyl-Nα-phenyl-L-phenylalaninamide, as a white solid; m.p. 107–108° C.

EXAMPLE 10

Prepared according to or similarily to the procedures described in the previous examples are the compounds listed in Table I.

TABLE I

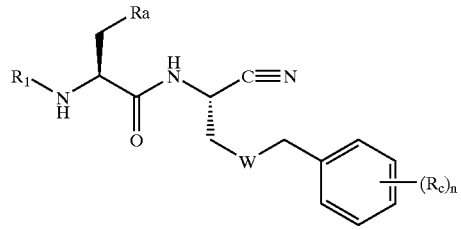

(R$_c$)$_n$ = substituents other than H

| Compound | R$_1$ | Ra | W | (R$_c$)$_n$ | m.p. (° C.)/MS |
|---|---|---|---|---|---|
| (1) | phenyl | 3-tolyl | O | 3-COOH | 135–137 |
| (2) | phenyl | 3-tolyl | CH$_2$ | 3-COOH | 146–148 |
| (3) | phenyl | phenyl | O | 3-COOH | foam |
| (4) | phenyl | 3-pyridyl | O | 3-COOH | MS: 445 (M + 1) |
| (5) | phenyl | 1-methyl-imidazol-4-yl | O | 3-COOH | MS: 448 (M + H) |
| (6) | 3-methoxy-carbonylphenyl | 3-tolyl | O | 3-COOH | 105–110° |
| (7) | 4-tolyl | 3-tolyl | O | 3-COOH | 88–93 |
| (8) | phenyl | 3-tolyl | O | 4-COOH | 177–178 |
| (9) | phenyl | thiazol-4-yl | O | 3-COOH | MS: 451 (M + 1) |
| (10) | phenyl | indol-3-yl | O | 3-COOH | MS: 481 (M − 1) |
| (11) | phenyl | 3-tolyl | O | — | MS: 414 (M + H) |
| (12)[1] | phenyl | 4-pyridyl | O | 3-COOH | 102–105 |
| (13) | phenyl | 3-tolyl | O | 3-CH$_2$OH | MS: 444 (M + H) |
| (14)[1] | phenyl | (3-methyl-7-azaindol-yl) | O | 3-COOH | 85 (dec) |
| (15) | 4-Cl-phenyl | 3-tolyl | O | 3-COOH | 80–82 |
| (16) | 3-Cl-phenyl | 3-tolyl | O | 3-COOH | 65–67 |
| (17) | 3-CF$_3$-phenyl | 3-tolyl | O | 3-COOH | 63–64 |
| (18) | 4-F-phenyl | 3-tolyl | O | 3-COOH | 61–62 |
| (19) | 2-tolyl | 3-tolyl | O | 3-COOH | 134–137 |
| (20) | 3-tolyl | 3-tolyl | O | 3-COOH | 78–80 |

TABLE I-continued

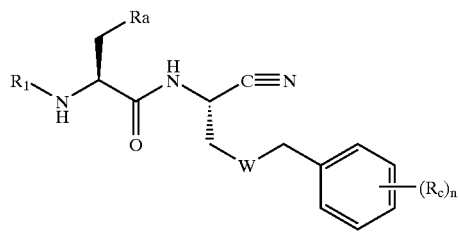

(R$_c$)$_n$ = substituents other than H

| Compound | R$_1$ | Ra | W | (R$_c$)$_n$ | m.p. (° C.)/MS |
|---|---|---|---|---|---|
| (21) | 6-methylbenzothiazol-2-yl | 3-tolyl | O | 3-COOH | 90–92 |
| (22) | 3,4-dichlorophenyl | 3-tolyl | O | 3-COOH | 95–97 |
| (23) | 3-cyanophenyl | 3-tolyl | O | 3-COOH | 82–84 |
| (24) | phenyl | 3-chlorophenyl | O | 3-COOH | 61–71 |
| (25) | 3-methoxyphenyl | 3-tolyl | O | 3-COOH | 70–73 |
| (26) | 5-methyl-1H-indol-2-yl | 3-tolyl | O | 3-COOH | 81–85 |
| (27) | 3-acetylphenyl | 3-tolyl | O | 3-COOH | 116–119 |
| (28) | phenyl | 3-methoxyphenyl | O | 3-COOH | 143–144 |
| (29) | 3-nitrophenyl | 3-tolyl | O | 3-COOH | 76–80 |
| (30) | 4-cyanophenyl | 3-tolyl | O | 3-COOH | 82–86 |
| (31) | 4-trifluoromethylphenyl | 3-tolyl | O | 3-COOH | 75–79 |
| (32) | 4-methylsulfonylphenyl | 3-tolyl | O | 3-COOH | 123–124 |
| (33) | phenyl | 2-methylfuran-5-yl | O | 3-COOH | |
| (34) | 5-methyl-3H-isobenzofuran-1-on-yl | 3-tolyl | O | 3-COOH | 100–103 |
| (35) | 3-methylsulfonylphenyl | 3-tolyl | O | 3-COOH | |
| (36) | 2-methylbenzoxazol-5-yl | 3-tolyl | O | 3-COOH | 92–100 |
| (37) | phenyl | 3-chlorophenyl | O | 3-COOH | 147–149 |
| (38) | phenyl | isopropyl | O | 3-COOH | |
| (39) | 2-acetylphenyl | 3-tolyl | O | 3-COOH | 180–181 |
| (40) | 3-trifluoromethylphenyl | isopropyl | O | 3-COOH | 63–65 |

TABLE I-continued ($R_c)_n$ = substituents other than H

| Compound | $R_1$ | Ra | W | $(R_c)_n$ | m.p. (° C.)/MS |
|---|---|---|---|---|---|
| (41) | 5-methyl-2-methyl-isoindole-1,3-dione | 3-tolyl | O | 3-COOH | 113–120 dec |
| (42) | 5-methyl-indan-1-one | 3-tolyl | O | 3-COOH | MS: 512 (M + H) |
| (43) | phenyl | cyclohexyl | O | 3-COOH | 131–135 |
| (44) | 5-methyl-2-acetyl-thiophene | 3-tolyl | O | 3-COOH | MS: 504 (M − H) |
| (45) | phenyl | 3-tolyl | O | 3-OH | MS: 430 (M + H) |
| (46) | 5-methyl-isobenzofuran-1(3H)-one | 3-chlorophenyl | O | 3-COOH | 95–97 |
| (47) | 3-CF$_3$-phenyl | 4-methoxyphenyl | O | 3-COOH | MS: 542 (M + H) |
| (48) | 3-tolyl | 4-methoxyphenyl | O | 3-COOH | MS: 488 (M + H) |
| (49) | 6-fluoro-3-tolyl | 4-methoxyphenyl | O | 3-COOH | MS: 506 (M + H) |
| (50) | 3,4-dicyano-phenyl | 3-tolyl | O | 3-COOH | 111–113 |
| (51) | 3-CF$_3$-phenyl | 2-thienyl | O | 3-COOH | MS: 518 (M + H) |
| (52) | 3-CF$_3$-5-OCH$_3$ phenyl | 3-tolyl | O | 3-COOH | MS: 556 (M + H) |
| (53) | 3-CF$_3$-5-F-phenyl | 3-tolyl | O | 3-COOH | 87–89 |
| (54) | 3,5-di-CF$_3$-phenyl | 3-tolyl | O | 3-COOH | 173–174 |
| (55) | 3-CF$_3$-phenyl | 5-methyl-2-furanyl | O | 3-COOH | 124 |
| (56) | 3-cyanophenyl | 5-methyl-2-furanyl | O | 3-COOH | 153 |
| (57) | 6-methyl-2-methyl-isoindolin-1-one | 3-totyl | O | 3-COOH | 147–153 |
| (58) | 3-ethoxycarbonyl-phenyl | 5-methyl-2-furanyl | O | 3-COOH | MS: 520 (M + H) |

TABLE I-continued (R_c)_n = substituents other than H

| Compound | R₁ | Ra | W | (R_c)_n | m.p. (° C.)/MS |
|---|---|---|---|---|---|
| (59) | 3-carboxyphenyl | 5-methyl-2-furanyl | O | 3-COOH | MS: 490 (M + H) |
| (60) | 3-CF₃-phenyl | 3-tolyl | CH₂ | 3-COOH | 81–83 |
| (61) | 5-methyl-3-oxo-1,3-dihydroisobenzofuran-1-yl | 3-tolyl | CH₂ | 3-COOH | 91–94 |
| (62) | 3-(pyrrolidino-carbonyl)phenyl | 3-tolyl | O | 3-COOH | 118–121 |
| (63) | 3-(dimethylamino-carbonyl)phenyl | 3-tolyl | O | 3-COOH | 106–108 |
| (64) | 3-(methylamino-carbonyl)phenyl | 3-tolyl | O | 3-COOH | 116–119 |
| (65) | 3-(dimethylamino-carbonyl)phenyl | 3-tolyl | O | 3-COOH | 120–122 |
| (66) | phenyl | 3-tolyl | O | 4-F, 3-COOH | 107–108 |
| (67) | 4-(pyrrolidino-carbonyl)phenyl | 3-tolyl | O | 3-COOH | 135–138 |
| (68) | 2-fluorophenyl | 3-tolyl | O | 3-COOH | 93–95 |
| (69) | 4-fluorophenyl | 3-tolyl | O | 3-COOH | 75–78 |
| (70) | phenyl | 3-tolyl | O | 3-(5-tetrazolyl) | 120–122 |
| (71) | 6-methyl-3-oxo-1,3-dihydroisobenzofuran-1-yl | 3-tolyl | O | 3-COOH | 100–102 |
| (72) | 1,1-dimethyl-5-methyl-3-oxo-1,3-dihydroisobenzofuran-1-yl | 3-tolyl | O | 3-COOH | 130–132 |
| (73) | 5-methyl-3-oxo-1,3-dihydroisobenzofuran-1-yl | 3-tolyl | O | 3-(5-tetrazolyl) | 130–133 |
| (74) | 5-methyl-1-oxo-1,3-dihydroisobenzofuran-3-yl | 3-tolyl | O | 3-COOH | 152–154 |

TABLE I-continued (R$_c$)$_n$ = substituents other than H

| Compound | R$_1$ | Ra | W | (R$_c$)$_n$ | m.p. (° C.)/MS |
|---|---|---|---|---|---|
| (75) | 5-methylphthalide | 3-tolyl | O | 4-F, 3-COOH | 119–122 |
| (76) | 4-fluorophenyl | 3-tolyl | O | 4-F, 3-COOH | 108–111 |
| (77) | 5-methylphthalide | 3-tolyl | O | 3-F, 4-COOH | 235–238 |
| (78) | phenyl | 3-tolyl | O | 3-F, 4-COOH | 161–164 |
| (79) | phenyl | 4-trifluoromethyl-phenyl | O | 3-COOH | 155–158 |
| (80) | phenyl | 3-tolyl | O | 4,6-F, 3-COOH | 91–93 |
| (81) | phenyl | 3-tolyl | O | 4-Cl, 3-COOH | 73–75 |
| (82) | phenyl | 3-tolyl | O | 2,4-F, 3-COOH | 158–159 |
| (83) | 3-pyridyl | 3-tolyl | O | 3-COOH | MS: 459 (M + H) |
| (84) | phenyl | 3-tolyl | O | 2-F, 3-COOH | 110–115 |

[1]CF$_3$COOH salt

EXAMPLE 11

Prepared according to or similarly to the procedures described in the previous examples are the compounds listed in Table II.

TABLE II

| Compound | R$_1$ | Ra | W | Het | m.p. (° C.)/MS |
|---|---|---|---|---|---|
| (1) | phenyl | 3-tolyl | CH$_2$ | 5-methylfuran-2-COOH | 165–167 |

TABLE II-continued

| Compound | R₁ | Ra | W | Het | m.p. (° C.)/MS |
|---|---|---|---|---|---|
| (2) | phenyl | 3-tolyl | O | furan-COOH | MS: 447 (M + H) |
| (3) | phenyl | 3-tolyl | O | thiazole-COOH | 134 |
| (4) | phenyl | 3-tolyl | O | pyridine-COOH | MS: 459 (M + H) |
| (5) | phenyl | 3-tolyl | O | thiophene-COOH | 86–88 |
| (6) | methyl-phthalide | 3-tolyl | O | thiophene-COOH | 112–115 |
| (7) | phenyl | 3-tolyl | O | pyridine-COOH | MS: 459 (M + H) |
| (8) | phenyl | 3-tolyl | O | 4-methylpyridine-COOH | 128 |

EXAMPLE 12

Prepared according to or similarily to the procedures described in the previous examples are the compounds listed in Table III.

TABLE III

| Compound | Ar | Ra | R₅ | m.p. (° C.)/MS |
|---|---|---|---|---|
| (a) | phenyl | 3-indolyl | ethyl | 67–70 |
| (b) | phenyl | 3-tolyl | ethyl | 96–97 |
| (c) | phenyl | phenyl | H | MS: 280 (M + H) |
| (d) | phenyl | 4-methoxyphenyl | H | 140–141 |
| (e) | phenyl | 3-benzothienyl | H | 110 |
| (f) | 3-CF₃-phenyl | phenyl | H | MS: 348 (M + H) |
| (g) | phenyl | 2-thienyl | H | 124 |

TABLE III-continued

![structure]

| Compound | Ar | Ra | $R_5$ | m.p. (° C.)/MS |
|---|---|---|---|---|
| (h) | 3-CF$_3$-phenyl | 3-indolyl | H | 108 |
| (i) | 4-t-butylphenyl | 3-indolyl | H | 104 |
| (j) | phenyl | cyclohexyl | H | 140–142 |
| (k) | phenyl | 4-methoxyphenyl | CH$_2$OH | MS: 340 (M + H) |
| (l) | 3-acetylphenyl | 3-tolyl | H | 152–153 |
| (m) | 3-ethoxycarbonyl-phenyl | 3-tolyl | H | 70–72 |
| (n) | 3-fluorophenyl | 3-tolyl | H | 93–95 |
| (o) | 3-CF$_3$-phenyl | benzyl | H | 102–104 |
| (p) | 3-CF$_3$-phenyl | 3-chlorophenyl | H | MS: 382 (M + H) |
| (q) | 3-CF$_3$-phenyl | 3,4-dichloro-phenyl | H | 122–124 |
| (r) | 3-CF$_3$-phenyl | 2-methylfuran-5yl | H | MS: 352 (M + H) |
| (s) | 3-fluorophenyl | 2-naphthyl | H | 146–148 |
| (t) | 4-(aminomethyl)-phenyl | 3-tolyl | H | MS: 323 (M + H) |
| (u) | ![methylisobenzofuranone] | 3-tolyl | H | 178–180 |
| (v) | 3-CF$_3$-phenyl | 2-naphthyl | H | 163–164 |
| (w) | 3-CF$_3$-phenyl | cyclohexyl | H | MS: 354 (M + H) |
| (x) | 3-CF$_3$-phenyl | 3-tolyl | H | 102–103 |
| (y) | 3-carboxyphenyl | 2-methylfuran-5yl | H | MS: 329 (M + H) |

EXAMPLE 13

(S,S)-N-Phenyl-(3-methylphenyl)-alanyl-O-(carboxymethyl)-m-tyrosine nitrile

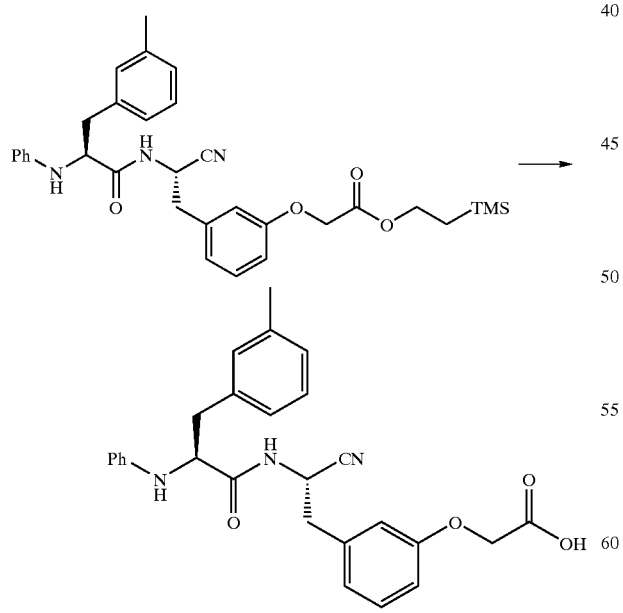

To a solution of (S,S)-N-phenyl-(3-methylphenyl)-alanyl-O-((2-trimethlysilylethoxy)-carbonyl-methyl)-m-tyrosine nitrile (260 mg) in THF (8 ml) at room temperature is added tetrabutyl ammonium formate (1 N in THF, 5 ml). The reaction mixture is stirred for 30 minutes and then ether (20 ml) and HCl (1 N, 20 ml) are added. The layers are separated and the organic layer is evaporated in vacuo. The residue is dissolved in ether (20 ml) and extracted with saturated NaHCO$_3$. The combined aqueous layers are acidified by addition of 1 N HCl and then extracted with ether. The combined organic layers are dried over Na$_2$SO$_4$ and evaporated in vacuo to provide the title compound as a solid. MS Found: M+1$^+$: 458; m.p. 63–65° C.

The starting material is prepared as follows:

t-Butyl 3-(hydroxymethyl)-phenoxyacetate

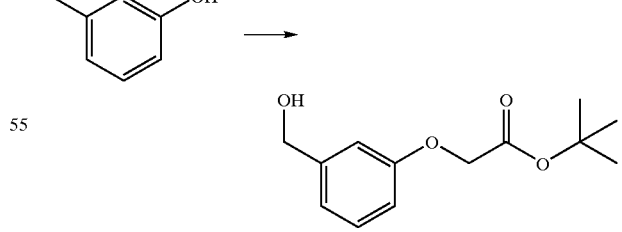

To a solution of 3-(hydroxymethyl)-phenol (50 g, 0.4 mol) and t-butyl bromoacetate (86 g, 0.44 mol) in DMF (500 ml, anhydrous) at room temperature is added K$_2$CO$_3$ (122 g, 0.88 mol). The reaction mixture is stirred vigorously for 2 hrs, and the mixture is poured into ice-water (2.5 L) and extracted with ether (3×500 ml). The combined ether extracts are washed with water, dried over MgSO$_4$ and evaporated in vacuo to provide t-butyl-3-(hydroxymethyl)-phenoxyacetate as a low melting, light yellow solid; mp: 52–56° C.

t-Butyl 3-(bromomethyl)-phenoxyacetate

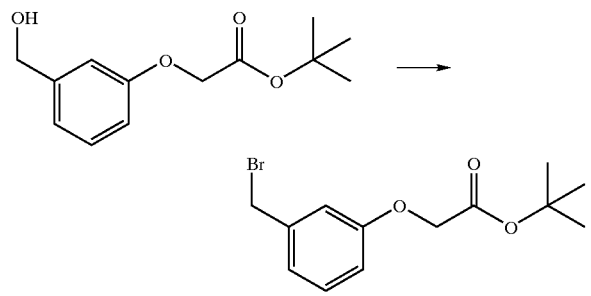

t-Butyl-3-(hydroxymethyl)-phenoxyacetate is dissolved in dichloromethane (1.3 L) at room temperature. Triphenylphosphine (127 g, 0.48 mol) is added with stirring, followed by dropwise addition of $CBr_4$ (146 g, 0.44 mol). The resultant mixture is stirred for 1 hour at room temperature and then evaporated in vacuo. The residue (553 g) is adsorbed onto silica-gel (100 g) and then placed on a sintered glass funnel containing 700 g of silica gel. The column is eluted with hexane (2×4000 L) followed by 4:1 hexane/EtOAc (2×4000L). The hexane/EtOAc solutions are combined and evaporated in vacuo to provide t-butyl 3-(bromomethyl)-phenoxyacetate as a colorless oil. MS Found: $M+18^+$:318, 320.

t-Butyl 3-(iodomethyl)phenoxy-acetate

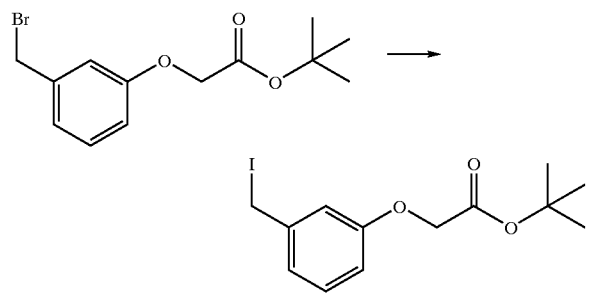

t-Butyl (3-bromomethyl)-phenoxy-acetate (65 g, 0.21 mol) is added to a suspension of NaI (163 g, 1.1 mol) in acetone (1 L) and the reaction mixture is stirred at room temperature overnight. The reaction mixture is filtered and the acetone evaporated in vacuo. The resultant orange oil is partitioned between dichloromethane and water. The organic layer is washed with $Na_2SO_3$ (5%, aq.), dried over $MgSO_4$ and then evaporated in vacuo to give t-butyl-3-(iodomethyl)-phenoxyacetate, which can be used without further purification. MS Found: $M+18^+$:366.

O-(t-Butoxycarbonyl-methyl)-m-tyrosine ethyl ester

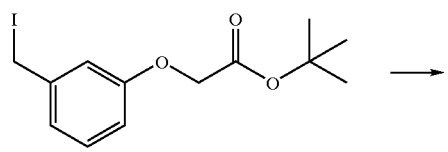

-continued

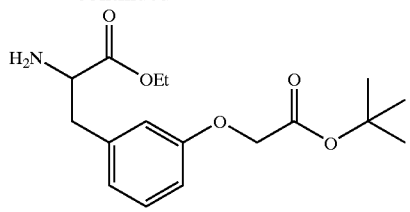

To a solution of freshly prepared LDA (0.22 mol.) in THF (200 ml, anhydrous, Aldrich) at −78° C. is added a solution of N-(diphenylmethylene)-glycine ethyl ester (52.6 g, 0.197 mol) in THF (280 ml), dropwise over 15 minutes. After stirring for 10 minutes, a solution of the iodide (68 g, 0.197 mol) in THF (280 ml) is added dropwise over 10 minutes. The resultant mixture is allowed to warm to room temperature and stirred for 1.5 hours. The reaction is quenched by the addition of saturated NaCl and the mixture is extracted with ether (3×250 ml). The combined organic phases are dried over $MgSO_4$ and evaporated in vacuo.

The resulting imine is stirred with 15% aqueous citric acid (1.0 L) in THF (10 L) at room temperature overnight. The mixture is extracted into ether (3×500 ml) and the combined organic layers are washed with $NaHCO_3$ (sat. aq.), dried with $MgSO_4$ and then evaporated in vacuo to give O-(t-butoxycarbonyl-methyl)-m-tyrosine ethyl ester as a light yellow oil. MS Found: $M+1^+$: 324, $2M+1^+$: 647.

(+/−)-N-Benzyloxycarbonyl-O-(t-butoxycarbonyl-methyl)-m-tyrosine Ethyl Ester

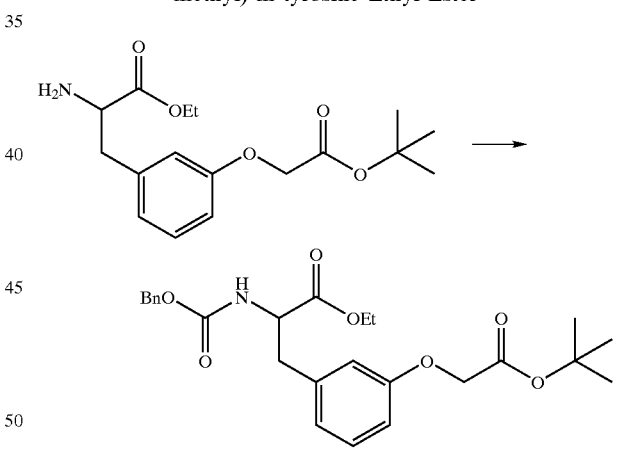

Benzyl chloroformate (22.9 ml, 0.16 mol) is added dropwise to solution of O-(t-butoxycarbonyl-methyl)-m-tyrosine ethyl ester (43.2 g, 0.133 mol) and N-methylmorpholine (20.6 ml, 0.19 mol) in dichloromethane (670 ml). The resulting mixture is allowed to warm to room temperature and then stirred for 1 hour. The mixture is extracted with $CH_2Cl_2$ (3×250 ml) and the combined organic layers are dried over $MgSO_4$ and evaporated in vacuo. The residue is chromatographed over Si-gel and eluted with Hexane/EtOAc 4:1. Evaporation of the solvents in vacuo yields N-benzyloxycarbonyl-O-(t-butoxycarbonyl-methyl)-m-tyrosine ethyl ester as a colorless oil. MS Found: $M+1^+$: 458, $M+18^+$: 475, $2M+18^+$: 932.

(S)-N-Benzyloxycarbonyl-O-(t-butoxycarbonyl-methyl)-m-tyrosine

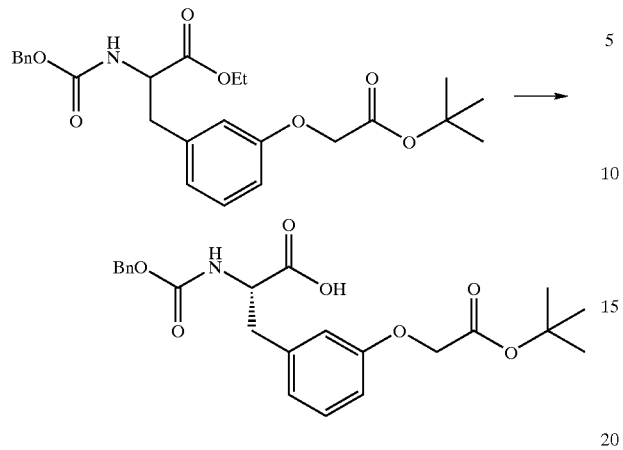

(+/−)-N-Benzyloxycarbonyl-O-(t-butoxycarbonyl-methyl)-m-tyrosine ethyl ester (44.7 g) is dissolved in acetonitrile (340 ml). To this solution is added NaHCO$_3$ (0.2 N, aq.), followed by an aqueous suspension of alcalase (4.3 ml). The mixture is stirred vigorously overnight and then the solvent is evaporated in vacuo. The resultant aqueous mixture is extracted with ether. The aqueous layer is acidified to pH 1 by the addition of aq. HCl (2 N) and then extracted with CH$_2$Cl$_2$. The combined CH$_2$Cl$_2$ layers are dried over MgSO$_4$ and the solvent removed in vacuo to give (S)-N-benzyloxycarbonyl-O-(t-butoxycarbonyl-methyl)-m-tyrosine as a colorless oil. MS Found: M+18$^+$: 475.

(S)-N-Benzyloxycarbonyl-O-(t-butoxycarbonyl-methyl)-m-tyrosine Amide

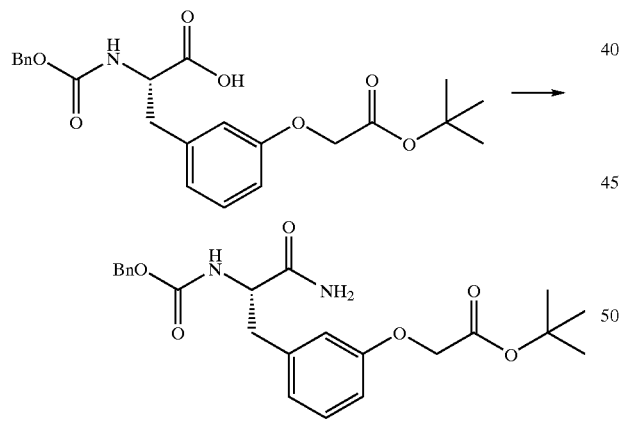

To a solution of above acid (19.3 g) and N-methylmorpholine (14.8 ml) in CH$_2$Cl$_2$ (180 ml) at −10° C. is added i-butyl chloroformate (7.0 ml) dropwise with an addition funnel. The resultant mixture is stirred for 15 minutes and then ammonia gas is bubbled through the mixture. The reaction is stirred for 2 hours and then cooled in an ice bath. HCl (1 N, aq.) is added to neutralize the excess ammonia. The mixture is extracted with CH$_2$Cl$_2$ and the combined organic layers are washed with NaHCO$_3$ (sat. aq.), dried over MgSO$_4$ and then evaporated in vacuo to yield the title compound as an oil. MS Found: M+1$^+$: 429.

(S)-N-Benzyloxycarbonyl-O-((2-trimethylsilylethoxy)-carbonyl-methyl)-m-tyrosine Amide

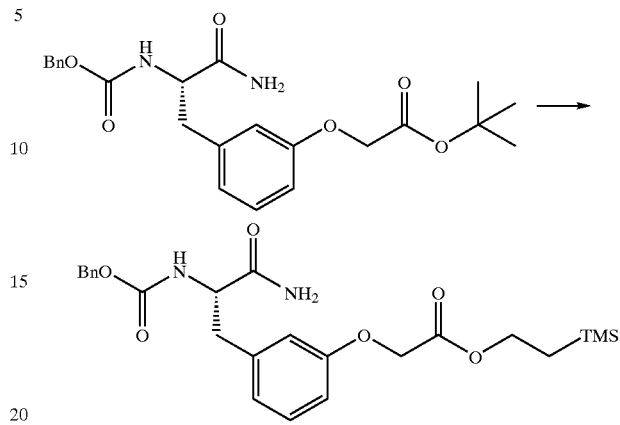

(S)-N-Benzyloxycarbonyl-O-(t-butoxycarbonyl-methyl)-m-tyrosine amide (5 g) is dissolved in TFA (25 ml) at room temperature. The mixture is stirred for 10 minutes and the TFA is removed in vacuo. The resultant acid is dissolved in acetonitrile (50 ml) and then 2-trimethylsilyl ethanol (1.4 g), dicyclohexyl carbodiimide (2.45 g) and 4-dimethylaminopyridine (670 mg) are added. The reaction mixture is stirred overnight and then filtered and evaporated in vacuo to provide the title compound which may be used without further purification. MS Found: M+1$^+$: 473, M+18$^+$: 490.

(S)-N-Benzyloxycarbonyl-O-((2-trimethylsilylethoxy)-carbonyl-methyl)-m-tyrosine Nitrile

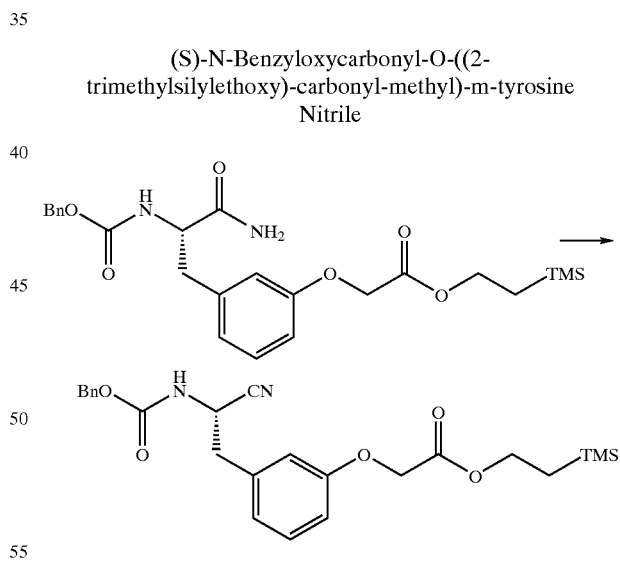

Oxalyl chloride (2.9 g) is added cautiously to DMF (75 ml) at 0° C. and the mixture is stirred at this temperature for 30 minutes. Pyridine (3.6 g) is added to the mixture, followed by a solution of (S)-N-Benzyloxycarbonyl-O-((2-trimethlysilylethoxy)-carbonyl-methyl)-m-tyrosine amide (5.4 g) in DMF (45 ml). The resulting mixture is stirred at 0° C. for 30 minutes and then diluted with EtOAc and water. The organic layer is washed with water and saturated NaCl, then dried over Na$_2$SO$_4$ and the solvents are removed in vacuo to give the title compound. MS Found: M+18$^+$: 472.

(S)-O-((2-Trimethylysilylethoxy)-carbonyl-methyl)-m-tyrosine Nitrile

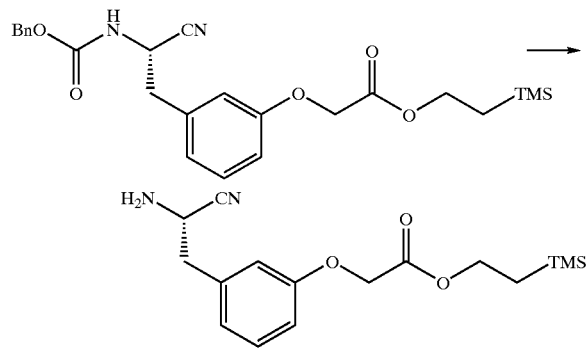

To a suspension of the above nitrile and 10% Pd/C (350 mg) in ethanol (100 ml) is added ammonium formate (7.2 g) and the mixture is stirred vigorously overnight at room temperature. The mixture is filtered and the solvents are removed in vacuo. The residue is partitioned between EtOAc and water and the organic layer is washed with water, sat. NaCl, dried over $Na_2SO_4$ and solvent is removed in vacuo to give the title compound. MS Found: $M+18^+$: 338, $2M+1^+$: 641.

(S,S)-N-Phenyl-(3-methylphenyl)-alanyl-O-((2-trimethylysilylethoxy)-carbonyl-methyl)-m-tyrosine Nitrile

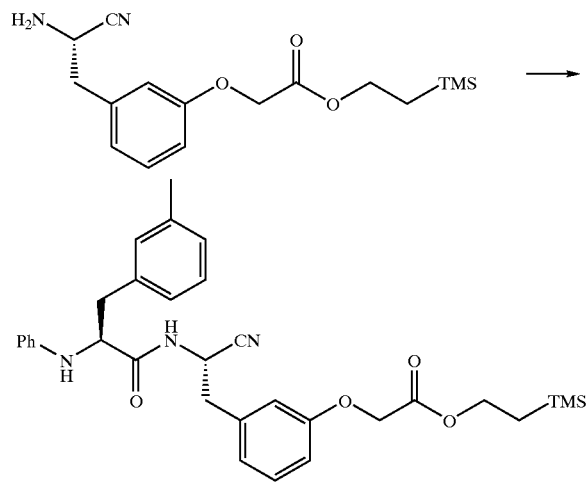

A solution of (S)-N-phenyl-(3-methylphenyl)-alanine (398 mg), N-methylmorpholine (583 mg) and TPTU (927 mg) in $CH_2Cl_2$ at room temperature is stirred for 10 minutes. To this mixture is added (S)-O-((2-trimethlysilylethoxy)-carbonylmethyl)-m-tyrosine nitrile (500 mg) and the reaction mixture is stirred at room temperature for 1 hour. The mixture is acidified by the addition of 1 N HCl and then extracted with $CH_2Cl_2$. The combined organic layers are dried over $MgSO_4$ and the solvents are removed in vacuo. The residue is chromatographed over silica-gel using 4:1 and then 2:1 hexane/EtOAc. The combined fractions with product at Rf 0.45 are evaporated in vacuo to provide the title compound. MS Found: $M+18^+$: 576.

EXAMPLE 14

Prepared according to or similarly to procedures described in the previous examples are:
- (a) N-[2-(3-carboxybenzyloxy)-1-(S)-cyanoethyl]-1-(phenylamino)-cyclohexanecarboxamide, m.p. 80–83° C.
- (b) N-(cyanomethyl)-Nα-(phenyl)-indan-2-yl-glycine-amide, m.p. 169–170° C.
- (c) N-(cyanomethyl)-Nα-(3-trifluoromethylphenyl)-indan-2-yl-glycineamide; MS:374 (M+H).

What is claimed is:

1. A compound of the formula

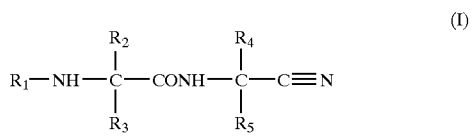

wherein $R_1$ is aryl or biaryl;

$R_2$ is aryl-lower alkyl, biaryl-lower alkyl, benzo-fused cycloakyl, cycloalkyl-lower alkyl, bicycloalkyl-lower alkyl, aryloxy-lower alkyl, or aryl-$C_2$-$C_7$-alkyl in which $C_2$-$C_7$-alkyl is interrupted by Y;

Y is O, S, SO, $SO_2$, CO or $NR_6$;

$R_3$ is hydrogen or lower alkyl; or $R_2$ and $R_3$ combined are $C_2$-$C_7$-alkylene or $C_2$-$C_7$-alkylene interrupted by Y;

$R_4$ is hydrogen or lower alkyl;

$R_5$ represents the grouping

in which X is lower alkylene, lower alkyleneoxy or $C_2$-$C_1$-alkylene interrupted by Y; Ar is monocyclic carbocyclic or monocyclic heterocyclic arylene; Q is a direct bond, lower alkylene, or thio- or oxy-lower alkylene: Z is hydroxy, acyloxy, carboxyl, or carboxyl derivatized as a pharmaceutically acceptable ester or amide; or Z is 5-tetrazolyl; Y is O, S, SO, $SO_2$ or $NR_6$; and $R_6$ is hydrogen, lower alkyl or aryl-lower alkyl; or a pharmaceutically acceptable salt thereof.

2. A compound according to claim 1 of the formula

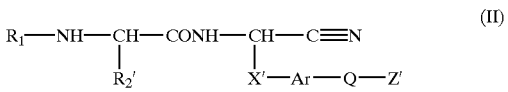

wherein $R_1$ is aryl or biaryl;

$R'_2$ aryl-lower alkyl, biaryl-lower alkyl, benzo-fused cycloalkyl, cycloalkyl-lower alkyl or bicycloalkyl-lower alkyl;

Ar is monocyclic carbocyclic or monocyclic heterocyclic arylene;

X' is lower alkylene or $C_2$-$C_7$-alkylene interrupted by O or S;

Q is a direct bond, lower alkylene, or thio- or oxy-lower alkylene; and

Z' is carboxyl, carboxyl derivatized as a pharmaceutically acceptable ester or amide, 5-tetrazolyl, or hydroxymethyl;

or a pharmaceutically acceptable salt thereof.

3. A compound according to claim 2 of formula II wherein $R_1$ is aryl; $R'_2$ is aryl-lower alkyl, X' is $C_1$-$C_3$-alkylene, or X' is $C_2$–$C_4$-alkylene interrupted by O or S; Ar is monocyclic carbocyclic arylene; Q is a direct bond, oxy-$C_1$–$C_4$-alkylene or $C_1$–$C_4$-alkylene; and Z' is carboxyl or carboxyl derivatized as a pharmaceutically acceptable ester; or a pharmaceutically acceptable salt thereof.

4. A compound according to claim 2 wherein $R_1$ is monocyclic carbocyclic aryl; $R'_2$ is carbocyclic aryl-methyl; X' is $C_1$–$C_3$-alkylene; or X' is $C_1$–$C_2$-alkylene interrupted by O; Ar is monocycliccarbocyclic arylene; Q is a direct bond or oxymethylene; Z is carboxyl, carboxyl derivatized as a pharmaceutically acceptable ester, or 5-tetrazolyl; or a pharmaceutically acceptable salt thereof.

5. A compound according to claim 2 of the formula

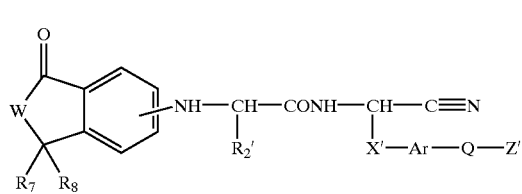

(IIa)

wherein $R'_2$, X', Ar, Q and Z' have meaning as defined in said claim; W represents O or $NR_6$ in which $R_6$ is lower alkyl; and $R_7$ and $R_8$ independently represent hydrogen or lower alkyl; or $R_7$ and $R_8$ together represent oxo; or a pharmaceutically acceptable salt thereof.

6. A compound according to claim 1 of the formula

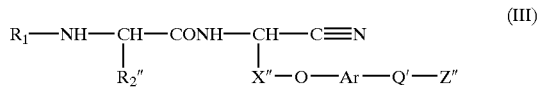

(III)

wherein $R_1$ is aryl or biaryl; $R''_2$ is aryl-lower alkyl, biaryl-lower alkyl, cycloalkyl-lower alkyl or bicycloalkyl-lower alkyl; Ar is monocyclic carbocyclic or monocyclic heterocyclic arylene; X" is lower alkylene; Q' is a direct bond or lower alkylene; Z" is carboxyl, carboxyl derivatized as a pharmaceutically acceptable ester, or 5-tetrazolyl; or a pharmaceutically acceptable salt thereof.

7. A compound according to claim 1 of the formula

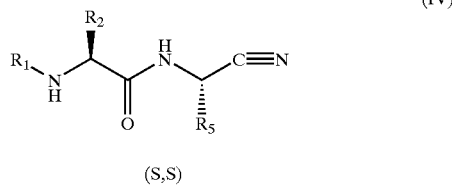

(IV)

(S,S)

wherein $R_1$, $R_2$ and $R_5$ have meaning as defined in said claim; or a pharmaceutically acceptable salt thereof.

8. A compound according to claim 2 of the formula

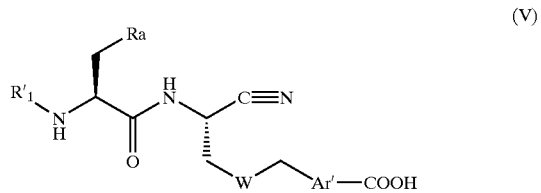

(V)

wherein $R'_1$ and Ra are aryl; W is O or $CH_2$; Ar' is arylene selected from pyridylene, furanylene, thienylene, thiazolylene, phenylene or phenylene substituted by 1 to 3 of alkyl or halo; a pharmaceutically acceptable salt thereof; or a pharmaceutically acceptable ester thereof.

9. A compound according to claim 8 wherein $R'_1$ and Ra are independently phthalidyl, phenyl, or phenyl mono-, di- or tri-substituted by lower alkyl, halo, trifluoromethyl, cyano, nitro, hydroxy, acyloxy, acyl, carboxyl, lower alkylsulfonyl, or esterified or amidated carboxyl; W is O; Ar' is 1,3-phenylene or 1,3-phenylene mono- or di-substituted by chloro or fluoro; a pharmaceutically acceptable salt thereof; or a pharmaceutically acceptable ester thereof.

10. A compound according to claim 8 wherein $R'_1$ is phthalidyl, phenyl, or phenyl mono- or disubstituted by halo, lower alkyl or esterified or amidated carboxyl, Ra is 3-tolyl; W is O; Ar' is 1,3-phenylene or 1,3-phenylene mono- or disubstituted by chloro or fluoro; a pharmaceutically acceptable salt thereof; or a pharmaceutically acceptable ester thereof.

11. A compound according to claim 8 wherein $R'_1$ is phenyl; Ra is 3-tolyl; W is O; Ar' is 1,3-phenylene or 1,3-phenylene mono- or disubstituted by chloro or fluoro; a pharmaceutically acceptable salt thereof; or a pharmaceutically acceptable ester thereof.

12. A method of inhibiting cysteine cathepsin activity in a mammal which comprises administering to a mammal in need thereof an effective cathepsin inhibiting amount of a compound of claim 1.

13. A method of treating cysteine cathepsin dependent conditions in a mammal which comprises administering to a mammal in need thereof an effective cysteine cathepsin inhibiting amount of a compound of claim 1.

14. A method of inhibiting cathepsin B activity in a mammal which comprises administering to a mammal in need thereof an effective cathepsin B inhibiting amount of a compound of claim 1.

15. A pharmaceutical composition comprising an effective cysteine cathepsin inhibiting amount of a compound of claim 1 in combination with one or more pharmaceutically acceptable carriers.

16. A process for the preparation of a compound of claim 1 which comprises (a) condensing a compound of the formula VI

(VI)

wherein $R_4$ and $R_5$ have meaning as defined in said claim, with an acid of formula VII

(VII)

wherein $R_1$, $R_2$ and $R_3$ have meaning as defined in said claim; or with a reactive derivative thereof; or (b) condensing a compound of the formula VIII

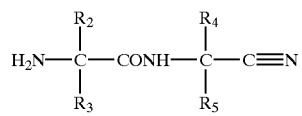 (VIII)

wherein $R_2$, $R_3$, $R_4$, and $R_5$ have meaning as defined in said claim, with a reactive aryl reagent corresponding to the group $R_1$, and in above processes, if required, temporarily protecting any interfering reactive groups and then isolating the resulting compound of the invention; and, if desired, converting any resulting compound into another compound of the invention; and/or if desired, converting a resulting compound into a salt or a resulting salt into the free acid or base or into another salt.

* * * * *